United States Patent
Swanson

(10) Patent No.: US 11,774,743 B2
(45) Date of Patent: Oct. 3, 2023

(54) FEW-MODE OPTICAL FIBER MEASUREMENT INSTRUMENT

(71) Applicant: Eric Swanson, Gloucester, MA (US)

(72) Inventor: Eric Swanson, Gloucester, MA (US)

(*) Notice: Subject to any disclaimer, the term of this patent is extended or adjusted under 35 U.S.C. 154(b) by 0 days.

(21) Appl. No.: 17/194,274

(22) Filed: Mar. 7, 2021

(65) Prior Publication Data

US 2021/0215927 A1  Jul. 15, 2021

Related U.S. Application Data

(63) Continuation of application No. 15/168,189, filed on May 30, 2016, now Pat. No. 10,969,571.

(51) Int. Cl.

| | |
|---|---|
| *G02B 23/24* | (2006.01) |
| *G02B 23/26* | (2006.01) |
| *G01B 9/02004* | (2022.01) |
| *A61B 5/00* | (2006.01) |
| *G02B 6/028* | (2006.01) |

(Continued)

(52) U.S. Cl.
CPC ...... *G02B 23/2469* (2013.01); *A61B 1/00163* (2013.01); *A61B 1/00165* (2013.01); *A61B 5/0066* (2013.01); *A61B 5/0084* (2013.01); *G01B 9/02004* (2013.01); *G01B 9/02091* (2013.01); *G02B 6/0288* (2013.01); *G02B 23/26* (2013.01); *A61B 1/00172* (2013.01); *A61B 1/07* (2013.01); *A61B 5/0071* (2013.01); *A61B 5/0075* (2013.01); *G01N 21/4795* (2013.01);
(Continued)

(58) Field of Classification Search
CPC .. G02B 23/2469; G02B 23/26; G02B 6/0288; G02B 6/2861; G01B 9/02004; G01B 9/0291; A61B 5/0066; A61B 5/0084; A61B 5/0071; A61B 5/0075; G01N 21/4795; G01N 21/65; G01N 2021/6484

See application file for complete search history.

(56) References Cited

U.S. PATENT DOCUMENTS

| | | |
|---|---|---|
| 5,062,150 A | 10/1991 | Swanson et al. |
| 5,212,743 A | 5/1993 | Heisman |

(Continued)

FOREIGN PATENT DOCUMENTS

| | | |
|---|---|---|
| AU | 1977597 A | 9/1997 |
| EP | 0971626 A1 | 1/2000 |

(Continued)

OTHER PUBLICATIONS

Rong et al., In-fiber quasi-Michelson interferometer with a core-cladding-mode fiber end-face mirror, Appl. Opt. 52, 1441-1447 (2013) (Year: 2013).*

(Continued)

*Primary Examiner* — Peter Radkowski
(74) *Attorney, Agent, or Firm* — Rauschenbach Patent Law Group, PLLC; Kurt Rauschenbach

(57) ABSTRACT

Disclosed herein are configurations for few-mode fiber optical endoscope systems employing distal optics and few-mode, double-clad or other optical fiber wherein the systems directing an optical beam to a sample via the optical fiber; collecting light backscattered from the sample; direct the backscattered light to a detector via the optical fiber; and detect the backscattered light; wherein the directed optical beam is single mode and the collected light is one or more higher order modes.

20 Claims, 9 Drawing Sheets

(51) Int. Cl.
*G01B 9/02091* (2022.01)
*A61B 1/00* (2006.01)
*G02B 6/28* (2006.01)
*A61B 1/07* (2006.01)
*G01N 21/47* (2006.01)
*G01N 21/65* (2006.01)
*G01N 21/64* (2006.01)

(52) U.S. Cl.
CPC ..... *G01N 21/65* (2013.01); *G01N 2021/6484* (2013.01); *G02B 6/2861* (2013.01)

(56) References Cited

U.S. PATENT DOCUMENTS

| | | | |
|---|---|---|---|
| 5,321,501 A | 6/1994 | Swanson | |
| 5,459,570 A | 10/1995 | Swanson | |
| 5,465,147 A | 11/1995 | Swanson | |
| 5,619,368 A | 4/1997 | Swanson | |
| 5,748,598 A | 5/1998 | Swanson et al. | |
| 5,784,352 A | 7/1998 | Swanson et al. | |
| 5,956,355 A | 9/1999 | Swanson | |
| 6,134,003 A | 10/2000 | Tearney | |
| 6,160,826 A | 12/2000 | Swanson | |
| 6,191,862 B1 | 2/2001 | Swanson | |
| 6,288,784 B1 | 10/2001 | Hitzenberger | |
| 6,445,939 B1 | 9/2002 | Swanson | |
| 6,485,413 B1 | 11/2002 | Boppart | |
| 6,501,551 B1 | 12/2002 | Tearney | |
| 6,552,797 B2 | 4/2003 | Swanson | |
| 6,564,087 B1 | 5/2003 | Piths | |
| 6,665,068 B1 | 12/2003 | Schoeppe et al. | |
| 6,947,648 B2 | 2/2005 | Swanson | |
| 6,891,984 B2 | 5/2005 | Peterson | |
| 7,061,618 B2 | 6/2006 | Mia et al. | |
| 7,366,365 B2 | 4/2008 | Carver | |
| 7,418,169 B2 | 8/2008 | Tearney et al. | |
| 7,447,408 B2 | 11/2008 | Bouma et al. | |
| 7,530,948 B2 | 5/2009 | Seibel | |
| 7,538,859 B2 | 5/2009 | Tearney et al. | |
| 7,809,225 B2 | 10/2010 | Bouma et al. | |
| 7,809,226 B2 | 10/2010 | Bouma et al. | |
| 7,843,572 B2 | 11/2010 | Tearney et al. | |
| 7,847,949 B2 | 12/2010 | Tearney et al. | |
| 7,864,822 B2 | 1/2011 | Bouma | |
| 7,889,348 B2 | 2/2011 | Tearney et al. | |
| 7,916,387 B2 | 3/2011 | Schmitt | |
| 7,925,133 B2 | 4/2011 | Bouma et al. | |
| 8,078,245 B2 | 12/2011 | Daly | |
| 8,149,418 B2 | 4/2012 | Tearney et al. | |
| 8,300,230 B2 | 10/2012 | Galle et al. | |
| 8,369,669 B2 | 2/2013 | Bouma et al. | |
| 8,384,907 B2 | 2/2013 | Tearney et al. | |
| 8,384,909 B2 | 2/2013 | Yun | |
| 8,416,818 B2 | 4/2013 | Bouma | |
| 8,437,007 B2 | 5/2013 | Flanders | |
| 8,515,221 B2 | 8/2013 | Flanders | |
| 8,676,013 B2 | 3/2014 | Bouma et al. | |
| 8,690,330 B2 | 4/2014 | Hacker et al. | |
| 8,711,364 B2 | 4/2014 | Brennan | |
| 8,760,663 B2 | 6/2014 | Tearney et al. | |
| 8,822,905 B2 | 9/2014 | Ryf | |
| 8,838,213 B2 | 9/2014 | Tearney et al. | |
| 8,854,629 B2 | 10/2014 | Frisken | |
| 8,994,954 B2 | 3/2015 | Minneman | |
| 9,008,142 B2 | 4/2015 | Minneman | |
| 9,044,164 B2 | 6/2015 | Hacker et al. | |
| 9,140,854 B2 | 9/2015 | Doerr | |
| 9,162,404 B2 | 10/2015 | Doerr | |
| 9,186,066 B2 | 11/2015 | Tearney et al. | |
| 9,186,067 B2 | 11/2015 | Tearney et al. | |
| 9,254,089 B2 | 2/2016 | Tearney et al. | |
| 9,304,121 B2 | 4/2016 | Tearney et al. | |
| 9,400,169 B2 | 7/2016 | Zhou | |
| 9,464,883 B2 | 10/2016 | Swanson et al. | |
| 9,513,276 B2 | 12/2016 | Tearney et al. | |
| 9,615,748 B2 | 4/2017 | Tearney et al. | |
| 9,664,615 B2 | 5/2017 | Bouma et al. | |
| 9,683,928 B2 | 6/2017 | Swanson | |
| 10,107,616 B2 | 10/2018 | Zhou | |
| 10,126,572 B2 | 11/2018 | Zhang et al. | |
| 10,132,610 B2 | 11/2018 | Swanson et al. | |
| 10,191,145 B2 | 1/2019 | Swanson | |
| 10,401,883 B2 | 9/2019 | Swanson et al. | |
| 10,416,288 B2 | 9/2019 | Swanson | |
| 10,895,525 B2 | 1/2021 | Swanson | |
| 10,907,951 B2 | 2/2021 | Avci | |
| 10,969,571 B2 | 4/2021 | Swanson | |
| 2005/0046932 A1 | 3/2005 | Lange et al. | |
| 2006/0164639 A1 | 7/2006 | Horn et al. | |
| 2006/0187537 A1 | 8/2006 | Huber et al. | |
| 2007/0121196 A1 | 5/2007 | Tearney et al. | |
| 2007/0233396 A1 | 10/2007 | Tearney et al. | |
| 2007/0282403 A1 | 12/2007 | Tearney et al. | |
| 2008/0008478 A1 | 1/2008 | Theis et al. | |
| 2008/0192248 A1 | 8/2008 | Carver | |
| 2010/0165335 A1 | 7/2010 | Tearney | |
| 2010/0262115 A1 | 10/2010 | Madiyalakan et al. | |
| 2010/0329670 A1 | 12/2010 | Essiambre et al. | |
| 2011/0137178 A1 | 6/2011 | Tearney et al. | |
| 2011/0218404 A1 | 9/2011 | Hirakawa | |
| 2012/0002971 A1 | 1/2012 | Doerr | |
| 2012/0093189 A1 | 4/2012 | Fattal et al. | |
| 2012/0099112 A1 | 4/2012 | Alphonse et al. | |
| 2012/0224165 A1 | 9/2012 | Swanson | |
| 2012/0224805 A1 | 9/2012 | Doerr | |
| 2012/0226118 A1 | 9/2012 | Delbeke et al. | |
| 2012/0302862 A1 | 11/2012 | Yun et al. | |
| 2013/0044974 A1 | 2/2013 | Doerr | |
| 2013/0066215 A1 | 3/2013 | Tearney et al. | |
| 2013/0209022 A1 | 8/2013 | Doerr | |
| 2014/0126902 A1 | 5/2014 | Swanson | |
| 2014/0126990 A1 | 5/2014 | Swanson | |
| 2014/0147079 A1 | 5/2014 | Doerr | |
| 2014/0160488 A1 | 6/2014 | Zhou | |
| 2014/0235948 A1 | 8/2014 | Mahalati et al. | |
| 2014/0376000 A1 | 9/2014 | Swanson | |
| 2014/0376001 A1 | 12/2014 | Swanson | |
| 2015/0085884 A1 | 3/2015 | Fontaine et al. | |
| 2016/0033406 A1 | 2/2016 | Ashraf et al. | |
| 2016/0206184 A1 | 7/2016 | Tearney et al. | |
| 2016/0231101 A1 | 8/2016 | Swanson et al. | |
| 2016/0357007 A1 | 12/2016 | Swanson | |
| 2017/0143196 A1 | 5/2017 | Liang et al. | |
| 2017/0205253 A1 | 7/2017 | Handerek | |
| 2017/0360297 A1 | 12/2017 | Yun et al. | |
| 2021/0149101 A1 | 5/2021 | Swanson | |

FOREIGN PATENT DOCUMENTS

| | | |
|---|---|---|
| EP | 0981733 | 11/2004 |
| EP | 0883793 | 11/2007 |
| EP | 1839375 | 4/2014 |
| JP | 2002-214127 A | 7/2002 |
| JP | 2004-105708 A | 4/2004 |
| WO | 90/08433 A1 | 7/1990 |
| WO | 91/05414 A1 | 4/1991 |
| WO | 95/33970 A1 | 12/1995 |
| WO | 95/33971 A1 | 12/1995 |
| WO | 97/01167 A1 | 1/1997 |
| WO | 97/32182 A1 | 9/1997 |
| WO | 98/35203 A2 | 8/1998 |
| WO | 98/38907 A1 | 9/1998 |
| WO | 00/42906 A3 | 1/2001 |
| WO | 2012088361 | 6/2012 |
| WO | 2014/088650 | 6/2014 |
| WO | 2014/089504 | 6/2014 |

OTHER PUBLICATIONS

Casaubieilh et al., Optical coherence tomography with a Fizeau interferometer configuration, Proceedings of SPIE vol. 5858 (SPIE, Bellingham, WA, 2005) (Year: 2005).*

(56) References Cited

OTHER PUBLICATIONS

Li etal, Few-mode fiber based optical sensors, Optics Express, V 23, N. 2, 2015, p. 1139. (Year: 2015).*
Francois Parnet, Julien Fade, and Mehdi Alouini, "Orthogonality breaking through few-mode optical fiber," Appl. Opt. 55, 2508-2520 (2016) (Year: 2016).*
Huang H, Milione G, Lavery MP, et al. Mode division multiplexing using an orbital angular momentum mode sorter and MIMO-DSP over a graded-index few-mode optical fibre. Scientific Reports. Oct. 2015;5:14931. DOI: 10.1038/srep14931. PMID: 26450398; PMCID: PMC4598738 (Year: 2015).*
Y. Weng and Z. Pan, "Orbital-Angular-Momentum-based Image Sensor using High Resolution Photoacoustic Tomography," in Advanced Photonics 2015, OSA Technical Digest (online) (Optical Society of America, 2015), paper SeS1B.3. (Year: 2015).*
Radu Ionicioiu, Sorting quantum systems efficiently Sci Rep. 2016; 6: 25356. Published online May 4, 2016. doi: 10.1038/srep25356 (Year: 2016).*
Baranek et al., Rotating vortex imaging implemented by a quantized spiral phase modulation J. Europ. Opt. Soc. Rap. Public. 8, 13017 (2013) (Year: 2013).*
Ramachandran et al., Optical vortices in fiber, Nanophotonics 2013; 2(5-6): 455-474 (Year: 2013).*
Choi et al., Scanner-free and wide-field endoscopic imaging by using a single multimode optical fiber, Phys Rev Lett. Nov. 16, 2012; 109(20): 203901. (Year: 2012).*
Matthew D. Risi, Houssine Makhlouf, Andrew R. Rouse, and Arthur F. Gmitro, "Analysis of multimode fiber bundles for endoscopic spectral-domain optical coherence tomography," Appl. Opt. 54, 101-113 (2015) (Year: 2015).*
Terashima M, Kaneda H, Suzuki T. The role of optical coherence tomography in coronary intervention. Korean J Intern Med. Mar. 2012;27(1):1-12. doi: 10.3904/kjim.2012.27.1.1. Epub Feb. 28, 2012. PMID: 22403493; PMCID: PMC3295975. (Year: 2012).*
Tetsu Asami et al.; Development of a Fiber-Optic Optical Coherence Tomography Probe for Intraocular Use. Invest. Ophthalmol. Vis. Sci. 2016;57(9):OCT568-OCT574. doi: https://doi.org/10.1167/iovs.15-18853. (Year: 2016).*
Runde, Daniel, Breuer, Stefan and Kip, Detlef. "Mode-selective coupler for wavelength multiplexing using LiNbO3:Ti optical waveguides" Open Physics, vol. 6, No. 3, 2008, pp. 588-592. https://doi.org/10.2478/s11534-008-0078-1 (Year: 2008).*
Sergio G. Leon-Saval, Nicolas K. Fontaine, Joel R. Salazar-Gil, Burcu Ercan, Roland Ryf, and Joss Bland-Hawthorn, "Mode-selective photonic lanterns for space-division multiplexing," Opt. Express 22, 1036-1044 (2014) (Year: 2014).*
K. Takiguchi, et al., "Integrated-optic variable delay line and its application to a low-coherence reflectometer". Optics Letters, Oct. 15, 2005, pp. 2739-2741, vol. 30, No. 20, Optical Society of America.
Mahmoud S. Rasras, et al., "Integrated resonance-enhanced variable optical delay lines", IEEE Photonics Technology Letters, Apr. 4, 2005, pp. 834-836, vol. 17, No. 4.
Leimeng Zhuang, et al., "Low-loss, high-index-contrast Si3N4/SiO2 optical waveguides for optical delay lines in microwave photonics signal processing", Optics Express, Oct. 17, 2011, pp. 23162-23170, vol. 19, No. 23.
J.P. Mack, et al., "Photonic Integrated Circuit Switch Matrix and Waveguide Delay Lines for Optical Packet Synchronization" ECOC 2008, Sep. 21-25, 2008, pp. 87-88, vol. 4, IEEE, Brussels, Belgium.
Jingya Xie, et al., "Seven-bit reconfigurable optical true time delay line based on silicon integration", Optics Express, Sep. 22, 2014, pp. 22707-22715 vol. 22, No. 19.
Hansuek Lee et al., "Ultra-low-loss optical delay line on a silicon chip", Nature Communications, May 2012, 7 pages.
Xiaolong Wang, et al., "Phase error corrected 4-bit true time delay module using a cascaded 2×2 polymer waveguide switch array" Applied Optics, Jan. 20, 2007, pp. 379-383 vol. 46, No. 3.

Maciej Wojtkowski, et al., "Ultrahigh-resolution, high-speed, Fourier domain optical coherence tomography and methods for dispersion compensation", Optics Express, May 31, 2004, pp. 2404-2422, vol. 12, No. 11.
Dierck Hillmann et al., "Common approach for compensation of axial motion artifacts in swept-source OCT and dispersion in Fourier-domain OCT", Optics Express, Mar. 12, 2012, pp. 6761-6776, vol. 20, No. 6.
Norman Lippok, et al., "Dispersion compensation in Fourier domain optical coherence tomography using the fractional Fourier transform". Optics Express, Oct. 8, 2012, pp. 23398-23413, vol. 20, No. 1.
Kaname Jinguji, et al., "Two-port optical wavelength circuits composed of cascaded Mach-Zehnder interferometers with point-symmetrical configurations", Journal of Lightwave Technology, Oct. 10, 1996, pp. 2301-2310, vol. 14 No. 10.
Xingchen Ji, et al., "On-chip tunable photonic delay line", APL Photonics, 2019, pp. 090803-1-0908037, 4doi 10.1063/1.5111164.
EunSeo Choi, et al., "All-fiber variable optical delay line for applications in optical coherence tomography: feasibility study for a novel delay line", Optics Express, Feb. 21, 2005, pp. 1334-1345, vol. 13, No. 4.
Hailong Zhou, et al., "All-in-one silicon photonic polarization processor", Nanophotonics, 2019, pp. 2257-2267, vol. 8, No. 12.
Fred Heismann, "Analysis of a Reset-Free Polarization Controller for Fast Automatic PolarizationStabilization in Fiber-optic Transmission Systems", Journal of Lightwave Technology, Apr. 1994, pp. 690-699, vol. 12, No. 4.
Reinhold Noe, et al., "Automatic endless polarization control with integrated-optical Ti:LiNbO3 polarization transformers", Reinhold Noe, Optics Letters, Jun. 1988, pp. 527-529, vol. 13, No. 6.
Tao Chu, et al., "Compact 1 Å~N thermo-optic switches based on silicon photonic wire waveguides", Optics Express, Dec. 12, 2005, pp. 10109-10114, vol. 13, No. 25.
Xiaoxi Wang, et al., "Compact high-extinction-ratio silicon photonic variable optical attenuators (VOAs)", Proceedings of the Conference on Lasers and Electro Optics (CLEO), 2 pages, Paper SW1N.7, 2017.
Reinhold Noe,et al, "Endless Polarization Control Systems for Coherent Optics", Journal of Lightwave Technology, Jul. 1988, pp. 1199-1208, vol. 6, No. 7.
Ansheng Liu, et al., "High-speed optical modulation based on carrier depletion in a silicon waveguide", Optics Express, Jan. 22, 2007, pp. 660-668, vol. 15, No. 2.
Niels Quack, et al., "MEMS-Enabled Silicon Photonic Integrated Devices and Circuits", IEEE Journal of Quantum Electronics, Feb. 2020, vol. 56, No. 1.
Christopher R. Doerr, et al., "Monolithic PDM-DQPSK receiver in silicon", 36th European Conference and Exhibition on Optical Communication 2010 3 pages.
Benjamin G. Lee, et al., "Silicon Photonic Switch Fabrics: Technology and Architecture", Journal of Lightwave Technology, DOI 10.1109/JLT.2018.2876828, 2018, 15 pages.
Xin Tu, et al., "State of the Art and Perspectives on Silicon Photonic Switches", Micromachines, 2019, 19 pages, vol. 10, No. 55, doi:103390/mi10010051.
Richard Soref, "Tutorial: Integrated-photonic switching structures", APL Photonics, Jan. 29, 2018, 19 pages, doi. org/10.1063/1.5017968.
Benjamin Koch, et al., "Versatile endless optical polarization controller/tracker/demultiplexer". Optics Express, Apr. 7, 2014, pp. 8259-8276, vol. 22, No. 7.
P. Velha, et al., "Wide-band polarization controller for Si photonic integrated circuits", Optics Letters, Dec. 15, 2016, pp. 5656-5659, vol. 41, No. 21.
B. Imran Akca, "Non-moving scanner design for OCT systems", Optics Express, Dec. 12, 2016, vol. 24, No. 25.
Meena Siddiqui, et al., "High-speed optical coherence tomography by circular interferometric ranging", Nature Photonics, Nature Photonics, Feb. 2018, vol. 12.

(56) References Cited

OTHER PUBLICATIONS

Luis A. Bru, et al., "Integrated optical frequency domain reflectometry device for characterization of complex integrated devices", Optics Express, Nov. 12, 2018, vol. 26, No. 23, doi:10.1364/OE.26.030000.

Kaicheng Liang, et al., "Cycloid Scanning for Wide Field Optical Coherence Tomography Endomicroscopy and Angiography in Vivo", Optica, Jan. 2018, pp. 36-43, vol. 5, No. 1.

U.S. Appl. No. 16/864,056, filed Apr. 30, 2020, USPTO.

U.S. Appl. No. 15/147,775, filed Dec. 8, 2016, USPTO.

Non-Final Office Action received for U.S. Appl. No. 15/168,189, dated Jun. 15, 2017, 29 pages.

Fujimoto et al., "Finalists for the European Inventor Award 2017", Available at https://www.epo.org/learning-events/europeaninventor/finalists/2017 /fujimoto.html, 2017, 4 pages.

Lemire-Renaud et al., "Double-Clad Fiber with a Tapered End for Confocal Endomicroscopy," Biomedical Optics Express, 2011, vol. 2, No. 11, 2011, pp. 2961-2972.

Leon-Saval et al., "Mode-Selective Photonic Lanterns for Space-Division Multiplexing", Optics Express, vol. 22, No. 1, 2014, 9 pages.

Madore et al., "Asymmetric Double-Clad Fiber Couplers for Endoscopy", Optics Letters, vol. 38, No. 21, Nov. 1, 2013, pp. 4514-4517.

Fontaine et al., "Few-Mode Fiber Wavelength Selective Switch with Spatial-Diversity and Reduced-Steering Angle," in Optical Fiber Communication Conference, OSA Technical Digest (online) (Optical Society of America, 2014), paper Th4A.7, pp. 3.

Marom et al., "Wavelength-Selective Switch with Direct Few Mode Fiber Integration," Optics Express, vol. 23, No. 5, 2015, pp. 5723-5737.

Final Office Action received for U.S. Appl. No. 15/168,189, dated Apr. 19, 2018, 22 pages.

Oh et al., "Optical Fibers for High-Resolution in vivo Microendoscopic Fluorescence Imaging", Optical Fiber Technology, vol. 19, 2013, pp. 760-771.

Yu et al., "Experimental Characterization of Rayleigh Backscattering in Few-Mode Fiber Using All-Fiber Photonic Lanterns", in Asia Communications and Photonics Conference 2015, OSA Technical Digest (online) (Optical Society of America, 2015), 3 pages.

Non-Final Office Action received for U.S. Appl. No. 15/168,189, dated Sep. 21, 2018, 14 pages.

Final Office Action received for U.S. Appl. No. 15/168,189, dated Jun. 13, 2019, 14 pages.

Reck et al., "Experimental Realization of Any Discrete Unitary Operator", Physical Review Letters, vol. 73, No. 1, Jul. 34, 1994, pp. 58-63.

Weng et al., "Single-End Simultaneous Temperature and Strain Sensing Techniques Based on Brillouin Optical Time Domain Reflectometry in Few-Mode Fibers", Optics Express, vol. 23, No. 7, 2015, pp. 9024-9039.

Non-Final Office Action received for U.S. Appl. No. 15/168,189, dated May 15, 2020, 13 pages.

Fujimoto et al., "Optical Coherence Tomography: An Emerging Technology for Biomedical Imaging and Optical Biopsy", Neoplasia, vol. 2, No. 1-2, 2000, pp. 9-25.

Ozdur et al., "Free-Space to Single-Mode Collection Efficiency Enhancement Using Photonic Lanterns," Optics Letters, vol. 38, No. 18, Sep. 15, 2013, pp. 3554-3557.

Ozdur et al., "Photonic-Lantern-Based Coherent LIDAR System", Optics Express, vol. 23, No. 4., 2015, pp. 5312-5316.

Qui et al., "Exploiting Few Mode-Fibers for Optical Time-Stretch Confocal Microscopy in the Short Near-Infrared Window", Optics Express, vol. 20, No. 22, 2012, pp. 24115-24123.

Schmitt, Joseph M., "Optical Coherence Tomography (OCT): A Review", IEEE Journal of Selected Topics in Quantum Electronics, vol. 5, No. 4, 1999, pp. 1205-1215.

Yu, Siyuan, "Manipulating Optical Vortices Using Photonic Integration", AAPPS Bulletin, vol. 25, No. 2, 2015, pp. 19-24.

Notice of Allowance received for U.S. Appl. No. 15/168,189, dated Dec. 11, 2020, 9 pages.

Guan et al.,"Mode-Group-Selective Photonic Lantern based on Integrated 3D Devices Fabricated by Ultrafst Laser Inscription", Optica Publishing Group, 3 pages.

Restriction Requirement received for U.S. Appl. No. 15/168,189, dated Mar. 24, 2017, 5 pages.

S. Yun, G. Tearney, J. de Boer, and B. E. Bouma, "Removing the depth-degeneracy in optical frequency domain imaging with frequency shifting," Opt. Express 12(20), 4822-4828 (2004).

B. J. Vakoc, S. H. Yun, G. J. Tearney, and B. E. Bouma, "Elimination of depth degeneracy in optical frequency-domain imaging through polarization-based optical demodulation," Opt. Lett. 31(3), 362-364 (2006).

M. Siddiqui, S. Tozburun, E. Z. Zhang, and B. J. Vakoc, "Compensation of spectral and RF errors in swept-source OCT for high extinction complex demodulation," Opt. Express 23, 5508-5520 (2015).

K.-S. Lee, P. Meemon, W. Dallas, K. Hsu, and J. P. Rolland, "Dual detection full range frequency domain optical coherence tomography," Opt. Lett. 35(7), 1058-1060 (2010).

B. Hofer, B. Považay, B. Hermann, A. Unterhuber, G. Matz, and W. Drexler, "Dispersion encoded full range frequency domain optical coherence tomography," Opt. Express 17(1), 7-24 (2009).

T.-H. Tsai, B. Potsaid, Y. K. Tao, V. Jayaraman, J. Jiang, P. J. S. Heim, M. F. Kraus, C. Zhou, J. Hornegger, H. Mashimo, A. E. Cable, and J. G. Fujimoto, "Ultrahigh speed endoscopic optical coherence tomography using micromotor imaging catheter and VCSEL technology," Biomed. Opt. Express 4(7), 1119-1132 (2013).

B. Baumann, W. Choi, B. Potsaid, D. Huang, J. S. Duker, and J. G. Fujimoto, "Swept source Fourier domain polarization sensitive optical coherence tomography with a passive polarization delay unit," Opt. Express 20(9), 10229-10241 (2012).

Z. Wang, H.-C. Lee, O. O. Ahsen, B. Lee, W. Choi, B. Potsaid, J. Liu, V. Jayaraman, A. Cable, M. F. Kraus, K. Liang, J. Hornegger, and J. G. Fujimoto, "Depth-encoded all-fiber swept source polarization sensitive OCT," Biomed. Opt. Express 5(9), 2931-2949 (2014).

B. H. Park, M. C. Pierce, B. Cense, and J. F. de Boer, "Jones matrix analysis for a polarization-sensitive optical coherencetomography system using fiber-optic components," Opt. Lett 29(21), 2512-2514 (2004).

H. Pahlevaninezhad, A. Lee, L. Cahill, S. Lam, C. MacAulay, and P. Lane, "Fiber-Based Polarization Diversity Detection for Polarization-Sensitive Optical Coherence Tomography," Photonics 1(4), 283-295 (2014).

T. S. Ralston, D. L. Marks, P. S. Carney, and S. A. Boppart, "Interferometric synthetic aperture microscopy," Nat. Phys. 3(2), 129-134 (2007).

J. Morgner, W. Drexler, F. Kärtner, X. Li, C. Pitris, E. Ippen, and J. G. Fujimoto, "Spectroscopic optical coherence tomography," Opt. Lett. 25(2), 111-113 (2000).

R. Huber, M. Wojtkowski, J. G. Fujimoto, J. Y. Jiang, and A. E. Cable, "Three-dimensional and C-mode OCT imaging with a compact, frequency swept laser source at 1300 nm," Optics Express 13(26), 10523-10538 (2005).

R. Huber, M. Wojtkowski, K. Taira, J. G. Fujimoto, and K. Hsu, "Amplified, frequency swept lasers for frequency domain reflectometry and OCT imaging: design and scaling principles," Optics Express 13(9), 3513-3528 (2005).

B. Potsaid, I. Gorczynska, V. J. Srinivasan, Y. L. Chen, J. Jiang, A. Cable, and J. G. Fujimoto, "Ultrahigh speed spectral / Fourier domain OCT ophthalmic imaging at 70,000 to 312,500 axial scans per second," Optics Express 16 (19), 15149-15169 (2008).

Marinko V. Sarunic, Brian E. Applegate, and Joseph A. Izatt, "Real-time quadrature projection complex conjugate resolved Fourier domain optical coherence Tomography", Optics Letters, vol. 31, No. 16, Aug. 15, 2006.

Jiefeng Xi, Li Huo, Jiasong Li and Xingde Li, "Generic real-time uniform K-space sampling method for high-speed swept-Source optical coherence tomography", Optics Express, vol. 18, No. 9, Apr. 26, 2010.

(56) References Cited

OTHER PUBLICATIONS

V. Jayaraman, G.D. Cole, M. Robertson, C. Burgner, D. John, A. Uddin and A. Cable, "Rapidly swept, ultra-widely-tunable 1060 nm MEMS-VCSELs", Electronics Letters, Oct. 11, 2012 vol. 48 No. 21.

G. J. Tearney, R. H. Webb, and B. E. Bouma, "Spectrally Encoded Confocal Microscopy", Optics Letters, vol. 23, No. 15, Aug. 1, 1998.

Chen D. Lu, Martin F. Kraus, Benjamin Potsaid, Jonathan J. Liu, WooJhon Choi, Vijaysekhar Jayaraman, Alex E. Cable, Joachim Hornegger, Jay S. Duker and James G. Fujimoto, "Handheld ultrahigh speed swept source optical coherence tomography instrument using a MEMs scanning mirror", Biomedical Optics Express, vol. 5, No. 1, Jan. 1, 2014.

V. D. Nguyen, N. Weiss, W. Beeker, M. Hoekman, A. Leinse, R. G. Heideman, T. G. van Leeuwen, and J. Kalkman, "Integrated-optics-based swept-source optical coherence tomography," Opt. Lett. 37(23), 4820-4822 (2012).

B. I. Akca, V. Nguyen, J. Kalkman, N. Ismail, G. Sengo, S. Fei, A. Driessen, T. G. van Leeuwen, M. Pollnau, K. Worhoff, and R. M. de Ridder, "Toward Spectral-Domain Optical Coherence Tomography on a Chip," IEEE J. Sel. Top. Quantum Electron. 18(3), 1223-1233 (2012).

V. D. Nguyen, B. I. Akca, K. Worhoff, R. M. De Ridder, M. Pollnau, T. G. van Leeuwen, and J. Kalkman, "Spectral domain optical coherence tomography imaging with an integrated optics spectrometer," Opt. Lett. 36, 1293-1295 (2011).

G. Yurtsever, B. Považay, A. Alex, B. Zabihian, W. Drexler, and R. Baets, "Photonic integrated Mach-Zehnder Interferometer with an on-chip reference arm for optical coherence tomography," Biomed. Opt. Express 5(4), 1050-1061 (2014).

G. Yurtsever, N. Weiss, J. Kalkman, T. G. van Leeuwen, and R. Baets, "Ultra-compact silicon photonic integrated interferometer for swept-source optical coherence tomography," Opt Lett. 39(17), 5228-5231 (2014).

B. I. Akca, B. Povazay, A. Alex, K. Worhoff, R. M. de Ridder, W. Drexler, and M. Pallnau, "Miniature spectrometer and beam splitter for an optical coherence tomography on a silicon chip", Optics Express, vol. 31, No. 14, Jul. 3, 2014.

Kyle Preston, Arthur Nitkowski, Nicolás Sherwood-Droz, Andrew Berkeley, Bradley S. Schmid, and Arsen R. Hajian, OCTANE: Optical Coherence Tomography Advanced Nanophotonic Engine, CLEO 2013 Technical Digest, Paper AW31.5, Jun. 9-14, 2013.

Daniel Neill, Luke Stewart, Huiping Li, Tom Killin, Fan Chen, Steve Frisken, Glenn Baxter, Simon Poole, "Compact polarization diverse receiver for biomedical imaging Applications", SPIE Proceedings, vol. 7891, Jan. 22, 2011.

Arthur Nitkowski, Kyle Preston, Nicolás Sherwood-Droz, Andrew Berkeley, Bradford B. Behr, Bradley S. Schmidt, and Arsen R. Hajian, "Nano Spectrometer for Optical Coherence Tomography", Imaging and Applied Optics Conference, Paper AM1B.3, (2013).

B. Imran Akca, "Spectral-Domain Optical Coherence Tomography on a Silicon Chip", PhD Thesis. University of Twente, (2012).

D. Culemann, A. Knuettel, and E. Voges, "Integrated optical sensor in glass for optical coherence tomography," IEEE J. Sel. Topics Quantum Electron., vol. 6, No. 5, pp. 730-734, Oct. 2000.

E. Margallo-Balbas,M. Geljon, G. Pandraud, and P. J. French, "Miniature 10 kHz thermo-optic delay line in silicon," Opt Lett., vol. 35, No. 23, pp. 4027-4029, Dec. 2010.

B. Imran Akca, Markus Pollnau, Kerstin Worhoff, Rene M. De Ridder, "Silicon Oxynitride Technology for Integrated Optical Solutions in Biomedical Applications", In: 13th International Conference on Transparent Optical Networks 2011, Jun. 26-30, 2011, Stockholm, Sweden.

G. Yurtsever, P. Dumon, W. Bogaerts, and R. Baets, "Integrated photonic circuit in silicon on insulator for Fourier domain optical coherence tomography," in Proc. SPIE, Opt. Coherence Tomography Coherence Domain Opt. Methods Biomed. XIV, vol. 7554, San Francisco, CA, 2010, pp. 1-5.

V. D. Nguyen, N. Ismail, F. Sun, K. Worhoff, T. G. van Leeuwen, and J. Kalkman, "SiON integrated optics elliptic couplers for Fizeau-based optical coherence tomography," IEEE J. Lightw. Technol., Oct. 1, 2010, pp. 2836-2842, vol. 28, No. 19.

Haitham Omran, Yasser M. Sabry, Mohamed Sadek, Khaled Hassan, Mohamed Y. Shalaby and Diaa Khalil, "Deeply-Etched Optical MEMS Tunable Filter for Swept Laser Source Applications", IEEE Photonics Technology Letters. vol. 26, No. 1, Jan. 2014.

Firooz Aflatouni, Behrooz Abiri, Angad Rekhi, and Ali Hajimiri, "Nanophotonic coherent imager", Optics Express, vol. 23, No. 4, doi: 10.1364/OE.23.005117, 2015.

Gyeong Cheol Park, Weiqi Xue, Elizaveta Semenova, Kresten Yvind, Jesper Mørk, and Il-Sug Chung, "III-V/SOI Vertical Cavity Laser with In-plane Output into a Si Waveguide", Paper W2A.17, Proceedings of the Optical Fiber Communication Conference, 2015.

K. Worhoff, C. G. H. Roeloffzen, R. M. de Ridder, A. Driessen, and P. V. Lambeck, "Design and application of compact and highly tolerant polarization-independent waveguides," IEEE J. Lightw. Technol., vol. 25, No. 5, pp. 1276-1282, May 2007.

S. K. Selvaraja, W. Bogaerts, P. Absil, D. Van Thourhout, and R. Baets, "Record low-loss hybrid rib/wire waveguides tor silicon photonic circuits," Group IV Photonics (2010).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon-on-insulator platform," Opt. Express 18(17), 18278-18283 (2010).

D. Vermeulen, S. Selvaraja, P. Verheyen, P. Absil, W. Bogaerts, D. Van Thourhout, and G. Roelkens, "Silicon-on-insulator polarization rotator based on a symmetry breaking silicon overlay," IEEE Photonics Technol. Lett. 24(5), 482 (2012).

A. Mekis, A. Dodabalapur, R. Slusher, and J. D. Joannopoulos, "Two-dimensional photonic crystal couplers for unidirectional light output," Opt. Lett. 25(13), 942-944 (2000).

L. Chen, C. R. Doerr, L. Buhl, Y. Baeyens, and R. A. Aroca, "Monolithically integrated 40-wavelength demultiplexer and photodetector array on silicon," IEEE Photonics Technol. Lett. 23(13), 869-871 (2011).

C. R. Doerr, L. Chen, D. Vermeulen, T. Nielsen, S. Azemati, S. Stulz, G. McBrien, X.-M. Xu, B. Mikkelsen, M. Givehchi, C. Rasmussen, and S. Y. Park, "Single-chip silicon photonics 100-Gb/s coherent transceiver," in Optical Fiber Communication Conference, (Optical Society of America, 2014), Th5C. 1.

M. Izutsu, S. Shikama, and T. Sueta, "Integrated optical SSB modulator/frequency shifter," IEEE J. Quant. Electron., vol. 2, No. 11, pp. 2225-2227, 1981.

D. Taillert, H. Chong, P. I. Borel, L. H. Frandsen, R. M. D. L. Rue, and R. Baets, "A compact two-dimensional grating coupler used as a polarization splitter", IEEE Photon. Tech. Lett., vol. 15, pp. 1249-1251, 2003.

R. Nagarajan and Others, "10 Channel, 100Gbit/s per Channel, Dual Polarization, Coherent QPSK, Monolithic InP Receiver Photonic Integrated Circuit", Optical Fiber Communication Conference Proceedings, p. OML7, 2011.

N. Dupuis, C. R. Doerr, L. Zhang, L. Chen, N. J. Sauer, P. Dong, L. L. Buhl, and D. Ahn, "InP-based comb generator for optical OFDM," J. Lightw. Technol., 2011.

S. Chandrasekhar and Xiang Liu, "Enabling Components for Future High-Speed Coherent Communication Systems", Optical Fiber Communication Conference Tutorial, 2011.

Chao Zhou, et al., Space-division multiplexing optical coherence tomography, Optics Express, Aug. 6, 2013, pp. 19219-19227 vol. 21, No. 16, DOI:10.1364/OE.21.019219.

Yongyan Huang, et al., Wide-field high-speed space-division multiplexing optical coherence tomography using an integrated photonic device, Biomedical Optics Express, Jul. 28, 2017, pp. 3856-3867, vol. 8, No. 8, DOI:10.1364/BOE.8.003856.

C. Boudoux, et al., Rapid wavelength-swept spectrally encoded confocal microscopy, Optics Express, Oct. 3, 2005, pp. 8214-8221, vol. 13, No. 20, OSA.

Dongyao Cui, et al., Multifiber angular compounding optical coherence tomography for speckle reduction, Optics Letter, Jan. 1, 2017, pp. 125-128, vol. 42, No. 1, Optical Society of America.

(56) References Cited

OTHER PUBLICATIONS

Daniel J. Fechtig, et al., Line-field parallel swept source MHz OCT for structural and functional retinal imaging, Biomedical Optics Express, Mar. 1, 2015, pp. 716-735, vol. 6, No. 3, OSA.
Simon Lemire-Renaud, et al., Double-clad fiber coupler for endoscopy, Optics Express, May 10, 2020, 9755-9764, vol. 18, No. 10, OSA.
Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.
Seen Young Ryu, et al., Combined system of optical coherence tomography and fluorescence spectroscopy based on double-cladding fiber, Optics Letters, pp. 2347-2349, Oct. 15, 2008, vol. 33, No. 20.
Juan Sancho-Dura, et al., Handheld multi-modal imaging for point-of-care skin diagnosis based on akinetic integrated optics optical coherence tomography, Biophotonics Journal, 2018, pp. 1-6, 2018, Wiley-VCH Verlag, GmbH & Co. KGaA Weinheim.
Tuqiang Xie, et al., Fiber-optic-bundle-based optical coherence tomography, Optics Letters, Jul. 15, 2005, pp. 1803-1805, vol. 30, No. 14.
Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.
Chao Zhou, et al., Space-division multiplexing optical coherence tomography, Optics Express, Aug. 12, 2013, pp. 19219-19227, vol. 21, No. 16, OSA.
G. Roelkens, D. Vermeulen, S. Selvaraja, Student Member, IEEE, R. Halir, W. Bogaerts, Member, IEEE, and D. Van Thourhout, "Grating-Based Optical Fiber Interfaces for Silicon-on-Insulator Photonic Integrated Circuits", IEEE Journal of Selected Topics in Quantum Electronics, vol. 17, No. 3, May/Jun. 2011.
Attila Mekis, Steffen Gloeckner, Gianlorenzo Masini, Adithyaram Narasimha, Member, IEEE, Thierry Pinguet, Subal Sahni, and Peter De Dobbelaere,"A Grating-Coupler-Enabled CMOS Photonics Platform". IEEE Journal of Selected Topics in Quantum Electronics, vol. 17, Issue 3, May/Jun. 2011.
Neil Na, Harel Frish, I-Wei Hsieh, Oshrit Harel, Roshan George, Assia Barkai, and Haisheng Rong, "Efficient broadband silicon-on-insulator grating coupler with low backreflection", Optics Letters, vol. 36, No. 11, Jun. 1, 2011.
Wissem Sfar Zaoui, Marfa Félix Rosa, Wolfgang Vogel, Manfred Berroth Jörg Butschke, and Florian Letzkus, "Cost-affective CMOS-compatible grating couplers with backside metal mirror and 69% coupling efficiency", Optics Express, vol. 20, No. 26, Dec. 10, 2012.
Vilson R. Almeida, Roberto R. Panepucci, and Michal Lipson, "Nanotaper for compact mode conversion", Optics Letters, vol. 28, No. 15, Aug. 1, 2003.
Anatol Khilo, Miloš A. Popović, Mohammad Araghchini, and Franz X. Kärtner, "Efficient planar fiber-to-chip coupler based on two-stage adiabatic evolution", Optics Express, vol. 18, No. 15, Jul. 19, 2010.
Long Chen, Christopher R. Doerr, Young-Kai Chen, and Tsung-Yang Liow, "Low-Loss and Broadband Cantilever Couplers Between Standard Cleaved Fibers and High-Index-Contrast Si3N4 or Si Waveguides", IEEE Photonics Technology Letters, vol. 22, No. 23, Dec. 1, 2010.
Alan Y. Liu, Chong Zhang, Justin Norman, Andrew Snyder, Dmitri Lubyshev,Joel M. Fastenau, Amy W. K. Liu, Arthur C. Gossard, and John E. Bowers, "High performance continuous wave 1.3 Im quantum dot lasers on silicon", Applied Physics Letters,104, 041104 (2014).
Jie Sun, Erman Timurdogan, Ami Yaacobi, Zhan Su, Ehsan Shah Hosseini, David B. Cole, and Michael R. Watts, "Large-Scale Silicon Photonic Circuits for Optical Phased Arrays", IEEE Journal of Selected Topics in Quantum Electronics, vol. 20, No. 4, Jul./Aug. 2014.

Jie Sun, Ehsan Shah Hosseini, Ami Yaacobi, David B. Cole, Gerald Leake, Douglas Coolbaugh, and Micheael R. Watts, "Two-dimensional apodized silicon photonic phased arrays", Optics Letters, vol. 39, No. 2, Jan. 15, 2014.
C. T. DeRose, R. D. Kekatpure, D. C. Trotter, A. Starbuck. J. R. Wendt, A. Yaacobi, M. R. Watts, U. Chettiar, N. Engheta, and P. S. Davids, "Electronically controlled optical beam-steering by an active phased array of metallic nanoantennas". Optics Express, vol. 21, No. 4, Feb. 25, 2013.
Jie Sun, Erman Timurdogan, Ami Yaacobi, Ehsan Shah Hosseini, and Michel R. Watts, "Large-scale nanophotonic phased array", Nature, vol. 493, Jan. 10, 2013.
Ami Yaacobi Erman Timurdogan, and Michael R. Watts, "Vertical emitting aperture nanoantennas", Optics Letters, vol. 37, No. 9, May 1, 2012.
J. K. Doylend, M. J. R. Heck, J. T. Bovington, J. D. Peters, L. A. Coldre, and J. E. Bowers, "Two-dimensional free-space beam steering with an optical phased array of silicon-on-insulator", Optics Express, vol. 19, No. 22, Oct. 24, 2011.
Karel Van Acoleyen, Hendrick Rogier, and Roel Baets, "Two-dimensional optical phased array antenna on silicon-on-insulator", Optics Express, vol. 18, No. 13, Jun. 21, 2010.
James A. Burns, Brian F. Aull, Chenson K. Chen, Chang-Lee Chen, Craig L. Keast, Jeffrey M. Knecht, Vyshanavi Suntharalingam, Keith Warner, Peter W. Wyatt, and Donna-Ruth W. Yost, "A Wafer-Scale 3-D Circuit Integration Technology", IEEE Transactions on Electronic Devices, vol. 53, No. 10, Oct. 2006.
Dirk Lorenser, C. Christian Singe, Andrea Curatolo, and David D. Sampson, "Energy-efficient low-Fresnel-number Bessel beams and their application in optical coherence tomography", Optics Letters, vol. 39, No. 3, Feb. 1, 2014.
Niklas Weber, Dominik Spether, Andreas Seifert, and Hans Zappe, "Highly compact imaging using Bessel beams generated by ultraminiaturized multi-micro-axicon systems", Journal of Optical Society of America A. vol. 29, No. 5, May 2012.
Z. Xie, B. Armbruster, and T. Grosjean, "Axicon on a gradient index lens (AXIGRIN): integrated otial bench for Bessel beam generation from a point-like source", Applied Optics, vol. 53, Issue 26, (2014).
G.S. Sokolovskii, V.V. Dudelev, S.N. Losev, K.K. Soboleva, A.G. Deryagin, K.A. Fedorovac, V.L Kuchinskii, W. Sibbett, E.U. Rafailov, "Bessel beams from semiconductor light sources", Progress in Quantum Electronics, vol. 38, No. 4, Jul. 2014.
F. Merola ; S. Coppola ; V. Vespini; S. Grilli; P. Ferraro ; D. Balduzzi; A. Galli; R. Puglisi, "Fabrication and test of polymeric microaxicons", Apr. 16-19, 2012, Proceedings of the SPIE, doi:10.1117/12.922572.
Paul Steinvurzel, Khwanchai Tantiwanichapan, Masao Goto, and Siddharth Ramachandran, "Fiber-based Bessel beams with controllable diffraction-resistant distance", Optics Letters, vol. 36, No. 23, 2011.
Cedric Blatter; Branislav Grajciar; Christoph M. Eigenwillig; Wolfgang Wieser; Benjamin R. Biedermann; Robert Huber; Rainer A. Leitgeb, "High-speed functional OCT with self-reconstructive Bessel illumination at 1300 nm", Proceedings of the SPIE, doi:10.1117/12.889669, Jun. 1, 2011.
James G. Fujimoto, Eric Swanson, Robert Huber, European Inventor Award 2017, Jun. 15, 2017, 3 pages. PRWeb.
Manon Rostykus, and Christophe Moser, "Compact lensless off-axis transmission digital holographic microscope," Opt Ex. 25(14), 16652-16659 (2017).
Damien Loterie, Demetri Psaltis, and Christophe Moser, "Bend translation in multimode fiber imaging," Opt. Ex. 25(6), 6263-6273 (2017).
Edgar E. Morales-Delgado, Demetri Psaltis, and Christophe Moser, "Two-photon imaging through a multimode fiber," Opt Ex. 23(25), 32158-32170 (2015).
Damien Loterie, Sebstianus A. Goorden, Demetrie Psaltis, and Christophe Moser, "Confocal microscopy through a multimode fiber using optical correlation," Opt. Lett. 40(24), 5754-5757 (2015).
Siddharth Sivankutty, Esben Ravn Andresen, Rosa Cossart, Geraud Bouwmans, Serge Monneret, and Herve Rigneault, Ultra-thin rigid endoscope: two-photon imaging through a graded-index.

(56) References Cited

OTHER PUBLICATIONS

Sean C. Warren, Youngchan Kim, James M. Stone, Claire Mitchell, Jonathan C. Knight, Mark A. A. Neil, Carl Paterson, Paul M. W. French, and Chris Dunsby, "Adaptive multiphoton endomicroscopy through a dynamically deformed multicore optical fiber using proximal detection," Opt. Ex. 24(19), 21474-21484 (2016).
Alexander Fertman and Dvir Yelin, "Image transmission through an optical fiber using real-time modal phase restoration," JOSAB 30(1), 149-157 (2013).
Mickael Mounaix, Hilton B. de Aguiar, and Sylvain Gigan, "Temporal recompression through a scattering medium via a broadband transmission matrix," ArXiv (2017).
S. M. Popoff, G. Lerosey, R. Carminati, M. Fink, A.C. Boccara, and S. Gigan, "Measuring the Transmission Matrix in Optics : An Approach to the Study and Control of Light Propagation in Disordered Media," Phys. Rev. Lett. 104(10), 100601-100605 (2010).
Jürgen W. Czarske, Daniel Haufe, Nektarios Koukourakis, and Lars Büttner, "Transmission of independent signals through a multimode fiber using digital optical phase conjugation," Opt. Ex. 24(13), 15128-15136 (2016).
J. M. Stone, H. A. C. Wood, K. Harrinton, and T. A. Birks, "Low index contrast imaging fibers," Opt. Lett. 42(8), 1484-1487 (2017).
Harry A. C. Wood, Kerrianne Harrington, James M. Stone, Tim A. Birks, and Jonathan C. Knight, "Quantitative characterization of endoscopic imaging fibers," Opt. Ex 25(3), 1985-1992 (2017).
Antonio M. Caravaca-Aguirre and Rafael Piestun, "Single multimode fiber endoscope," Opt Ex. 25(3), 1656-1665 (2017).
Ivan Gusachenko, Mingahou Chen, and Kishan Dholakia, "Raman imaging through a single multimode fibre," Opt. Ex. 25(12), 13782-13798 (2017).
Tomas Cizmar, and Kishan Dholakia, "Shaping the light transmission through a multimode optical fibre: complex transformation analysis and applications in biophotonics," Opt Ex. 19(20), 18871-18884 (2011).
Moussa N'Gom, Theodore B. Norris, Eric Michielssen, Raj Rao Nadakuditi, "Mode Control in a Multimode Fiber Through Acquiring its Transmission Matrix from a Reference-less Optical System," ArXiv (2017).
Roberto Di Leonardo and Silvio Bianchi, "Hologram transmission through multi-mode optical fibers," Opt. Ex. 19(1), 247-254 (2011).
Carmelo Rosales-Guzman, Nkosiphile Bhebhe, Nyiku Mahonisi, and Andrew Forbes, "Multiplexing 200 modes on a single digital hologram," ArXiv (2017).
Peng Lu, Matthew Shipton, Anbo Wang, Shay Soker, and Yong Xu, "Adaptive control of waveguide modes in a two-mode fiber," Opt. Ex. 22(3), 2955-2964 (2014).
Shamir Rosen, Doron Gilboa, Ori Katz, Yaron Silberberg, "Focusing and Scanning through Flexible Multimode Fibers without Access to the Distal End", 8 pages.
Pablo Eugui, Antonia Lichtenegger, Marco Augustin, Danielle J. Harper, Martina Muck, Thomas Roetzer, Andreas Nartak, Thomas Konegger, Georg Widhalm, Christoph K. Hitzenberger, Adelheid Woehrer, and Bernhard Baumann, Beyond backscattering: Optical neuroimaging by BRAD, arXiv:1712.00361 -v1 [physics.optics] Dec. 1, 2017.
Carmelo Rosales-Guzmán and Andrew Forbes, "How to Shape Light with Spatial Light Modulators", SPIE Spotlight, doi: http://dx.doi.org/10.1117/3.2281295, 2017.
Lucas B. Soldano and Erik C. M. Pennings, "Optical Multi-Mode Interference Devices Based on Self-Imaging: Principles and Applications", Journal of Lightwave Technology, vol. 13, No. 4, Apr. 1995.
Victor Arrizón, Ulises Ruiz, Rosibel Carrada, and Luis A. Gonzalez, "Pixelated phase computer holograms for the accurate encoding of scalar complex fields", J Opt. Soc. Am. A/vol. 24, No. 11/Nov. 2007.
Jeff Demas, Lars Rishøj, and Siddharth Ramachandran*, Free-space beam shaping for precise control and conversion of modes in optical fiber,vol. 23, No. 22 DOI:10.1364/OE.23.028531, 2015.

S. M. Popoff, G. Lerosey, R. Carminati, M. Fink, A.C. Boccara, S. Gigan , "Measuring the Transmission Matrix in Optics: An Approach to the Study and Control of Light Propagation in Disordered Media", arXiv:0910.5436v2 [physics. optics] Jan. 18, 2010.
Hitzenberger, Christoph K., et at., In Vivo Intraocular Ranging By Wavelength Tuning Interferometry, SPIE, pp. 47-51, vol. 3251, retrieved from: http://proceedings.spiedigitallibrary.org/ on Sep. 24, 2013.
Warren L. Stutzman and Gary A. Thiele, "Antenna Theory and Design", John Wiley & Sons, ISBN 0-471-04458-X, 1981. Textbook.
Y. Zhao, Z. Chen, C. Saxer, S. Xiang, J.F. de Beor, and J.S. Nelson, "Phase-resolved optical coherence tomography and optical Doppler tomography for imaging blood flow in human skin with fast scanning speed and high velocity sensitivity," Opt. Lett. 25(2), 114-116 (2000).
W. Choi, B. Potsaid, V. Jayaraman, B. Baumann, I. Grulkowski, J. J. Liu, C. D. Lu, A. E. Cable, D. Huang, J. S. Duker, and J.G. Fujimoto, "Phase sensitive swept-source optical coherence tomography imaging of the human retina with a vertical cavity surface-emiting laser light source," Opt. Lett. 38(3), 338-340 (2013).
Youxin Mao, Costel Flueraru, Shoude Chang, Dan P. Popescu, Michael G. Sowa, "Preormance analysis of a swept-source optical coherence tomography system with a quadrature interferometer and optical amplification", Optics Communications, vol. 284, Issues 10-11, May 15, 2011.
C.M. Eigenwillig, B. R. Biedermann, G. Palte, and R. Huber, "K-space linear Fourier domain mode locked laser and applications for optical coherence tomography," Optics Express 16(12), 8916-8937 (2008).
Yizheng Zhu, Neil G. Terry, and Adam Wax, "Scanning fiber angle-resolved low coherence interferometry", Optics Letters, vol. 34, No. 20, 2009.
Michael Giacomelli, Yizheng, Zhu, John Lee, Adam Wax, "Size and shape determination of spheroidal scatters using two-dimensional angle resolved scattering",Optics Express, vol. 18, No. 14, 2010.
Humle, J.C. et al., "Fully integrated hybrid silicon free-space beam steering source with 32 channel phased array" International Society for Optics and Photonics (SPIE PW), San Francisco, CA Feb. 1-6, 2014, pp. 898907-1-898907-15.
Kevin Gourley, Ilya Golu, Brahim Chebbi, "First experimental demonstration of a Fresnel Axicon", Proceedings of the SPIE, doi:101117/12.807162, Jun. 18, 2008.
Oto Brzobohatý, TomášCižmár, and Pavel Zemánek, "High quality quasi-Bessel beam generated by round-tip axicon", Optics Express, vol. 16, No. 17, 2008.
S. Yerolatsitis, I. Gris-Sánchez, T. A. Birks, "Tapered Mode Multiplexers for Single Mode to Multi Mode Fibre Mode Transitions", Proceedings of the Optical Fiber Communications Conference, Paper w3B.4, 2015.
A. M. Velazquez-Benitez, J. C. Alvarado, G. Lopez-Galmiche, J. E. Antonio-Lopez, J. Hernández-Cordero, J. Sanchez-Mondragon, P. Sillard, C. M. Okonkwo, and R. Amezcua-Correa, "Six mode selective fiber optic spatial multiplexer", Optics Letters, vol. 40, No. 8, Apr. 15, 2015.
Bernard Oduro, Rand Ismaeel, Timothy Lee and Gilberto Brambilla, "Selective Excitation of High Order Modes in Few Mode Fibres Using Optical Microfibres", Proceedings of the Optical Fiber Communications Conference, Paper M3D.5, 2015.
S. U. Alam*, Y. Jung, Q. Kang, F. Poletti, J.K. Sahu and D. J. Richardson, "Recent Progress in the Development of Few Mode Fiber Amplifiers", Proceedings of the Optical Fiber Communications Conference, Paper Tu3C.1, 2015.
R. Ryf, N. K. Fontaine1, M. Montoliu, S. Randell, B. Ercan, H. Chen, S. Chandrasekhar, A. H. Gnauck, S. G. Leon-Saval, J. Bland-Hawthorn, J. R. Salazar-Gil, Y. Sun, R. Lingle, Jr., "Photonic-Lantern-Based Mode Multiplexers for Few-Mode-Fiber Transmission", Proceedings of the Optical Fiber Communications Conference, Paper W4J.2., 2015.
Sergio G. Leon-Saval, Nicolas K. Fontaine, Joel R. Salazar-Gil, Burcu Ercan, Roland Ryf, and Joss Bland-Hawthorn, "Mode-selective photonic lanterns for space division multiplexing", Optics Express, vol. 22, No. 1 Jan. 13, 2014.

(56) References Cited

OTHER PUBLICATIONS

Haoshuo Chen, Nicolas K. Fontaine, Roland Ryf, Binbin Guan, S. J. Ben Yoo, and Ton (A. M. J.) Koonen, "Design Constraints of Photonic-Lantem Spatial Multiplexer Based on Laser-Inscribed 3-D Waveguide Technology", Journal of Lightwave Technology, vol. 33, No. 6, Mar. 15, 2015.

Haoshuo Chen, Roy van Uden, Chigo Okonkwo, and Ton Koonen, "Compact spatial multiplexers for mode division multiplexing", Optics Express, vol. 22, No. 26, Dec. 26, 2014.

Simon Schneider, Matthias Lauermann, Philipp-Immanuel Dietrich, Claudius Weimann, Wolfgang Freude, and Christian Koos, Optical coherence tomography system mass producible on a silicon photonic chip, Optics Express, vol. 24, No. 2, Jan. 2016.

Eduardo Margallo-Balb'as, Gregory Pandraud and Patrick J. French, "Miniature Optical Coherence Tomography System Based on Silicon Photonics", SPIE 2Proceedings, vol. 6847 (2008).

Christopher R. Doerr and Lawrence L. Buhl, "Circular Grating Coupler for Creating Focused Azimuthally and Radially Polarized Beams", Optics Letters, vol. 36, No. 7, Apr. 1, 2011.

Nenad Bozinovic, Yang Yue, Yongxiong Ren, Moshe Tur, Poul Kristensen, Hao Huang, Alan E. Willner, Siddharth Ramachandran, "Terabit-Scale Orbital Angular Momentum Mode Division Multiplexing in Fibers", Science Magazine, vol. 340 Jun. 28, 2013.

D. Huang. E. A. Swanson, C. P. Lin, J. S. Schuman, W. G. Stinson, W. Chang, M. R. Hee, t. Flotte, K. Gregory, C. A. Puliafito and J. G. Fujimoto, "Optical coherence tomography," Science 254(5035), 1178-1181 (1991).

R. Leitgeb, C. Hitzenberger, and A. Fercher, "Performance of fourier domain vs. time domain optical coherence tomography," OPt. Express 11(8), 889-894 (2003).

J. F. de Boer, B. Cense, B. H, Park, M. C. Pierce, G. J. Tearney, and B. E. Bouma, "Improved signal-to-noise ratio in spectral-domain compared with time-domain optical coherence tomography," Opt. Lett. 28(21), 2067-2069 (2003).

M. Choma, M. Sarunic, C. Yang, and J. Izatt, "Sensitvity advantage of swept source and fourier domain optical coherence tomography," Opt. Express 11(18), 2183-2189 (2003).

M. Wojtkowski, A, Kowalczyk, R. Leitgeb, and A. F. Fercher, "Full range complex spectral optical coherence tomography technique in eye imaging," Opt. lett. 27(16), 1415-1417 (2002).

A. F. Fercher, C. K. Hitzenberger, G. Kamp, and S. Y. El-Zaiat, "Measurement of intraocular distances by backsattering spectral interferometry," Opt. Commun. 117(1), 43-48 (1995).

S. R. Chinn, E. A. Swanson, and J. G. Fujimoto, "Optical cohoerence tomography using a frequency-tunable optical source," Opt. Lett. 22(5), 340-342 (1997).

S. Yun, G. Tearney, J. de Boer, N. Iftima, and B. Bouma, "High-speed optical frequency-domain imaging," Opt. Express 11(22), 2953-2963 (2003).

R. Huber, M. Wojtkowski, and J.G. Fujimoto, "Fourier Domain Mode Locking (FDML): A new laser operating regime and applications for optical coherence tomography," Opt Express 14(8), 3225-3237 (2006).

R. Huber, D. C. Adler, and J. G, Fujimoto, "Buffered Fourier domain mode locking: unidirectional swept laser sources for optical coherence tomography imaging at 370,000 lines/s," Opt. Lett.31(20), 2975-2977 (2006).

B. Potsaid, V. Jayaraman, J. G. Fujimoto, J. Jiang, P. J. Heim, and A. E. Cable, "MEMS tunable VCSEL light source tor ultrahigh speed 60kHz-1MHz axial scan rate and long range centimeter class OCT imaging," in SPIE BiOS, (International Society for Optics and Photonics), (2012).

V. Jayaraman, G. D. Cole, M. Robertson, A. Uddin, and A. Cable, "High-sweep-rate 1310 nm MEMS-VCSEL with 150 nm continuous tuning range," Electron. Lett. 48(14), 867-869 (2012).

W. Wieser, W. Draxinger, T. Klein, S. Karpf, T. Pfeiffer, and R. Huber, "High definition live 3D-OCT in vivo: design and evaluation of a 4D OCT engine with 1 GVoxel/s," Biomed. Opt. Express 5(9), 2963-2977 (2014).

M.V. Sarunic, B.E. Applegate, and J.Izatt, "Real-Time Quadrature Projection Complex Conjugate Resolved Fourier Domain Optical Coherence Tomography," Optics Letters, vol. 31, No. 16, Aug. 15, 2006.

R. K. Wang, S. L. Jacques, Z. Ma, S. Hurst, S. R. Hanson, and A. Gruber, "Three dimensional optical angiography," Opt Express 15(7), 4083-4097 (2007).

Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Opt. Express 20 (4), 4710-4725 (2012).

S. Makita, Y. Hong, M. Yamanari, T. Yatagai, and Y. Yasuno, "Optical coherence angiography," Opt. Express 14(17), 7821-7840 (2006).

S. Yazdanfar, M. Kulkarni, and J. Izatt, "High resolution imaging of in vivo cardiac dynamics using color Doppler optical coherence tomography," Opt. Express 1(13), 424-431 (1997).

B. Vakoc, S. Yun, J. de Boer, G. Tearney, and B. Bouma, "Phase-resolved optical frequency domain imaging," Opt. Express 13(14), 5483-5493 (2005).

M. R. Hee, E. A. Swanson, J. G. Fujimoto, and D. Huang, "Polarization-sensitive low-coherence reflectometer for birefringence characterization and ranging," J. Opt. Soc. Am. B 9(6), 903-908 (1992).

J. F. de Boer and T. E. Milner, "Review of polarization sensitive optical coherence tomography and Stokes vector determination," J. Biomed Opt. 7(3), 359-371 (2002).

M. Pircher, C. K. Hitzenberger, and U. Schmidt-Erfurth, "Polarization sensitive optical coherence tomography in the human eye," Prog. Retin. Eye. Res. 30(6), 431-451 (2011).

S. K. Nadkarni, M. C. Pierce, B. H. Park, J. F. de Boer, P. Whittaker, B. E. Bouma, J. E. Bressner, E. Halpern, S. L. Houser, and G. J. Tearney, "Measurement of Collagen and Smooth Muscle Cell Content in Atherosclerotic Plaques Using Polarization-Sensitive Optical Coherence Tomography," J. Am. Coll. Cardiol. 49(13), 1474-1481 (2007).

B. R. Biedermann, W. Wieser, C. M. Eigenwillig, T. Klein, and R. Huber, "Dispersion, coherence and noise of Fourier domain mode locked lasers," Opt. Express 17(12), 9947-9961 (2009).

M. Sarunic, M. A. Choma, C. Yang, and J. A. Izatt, "Instantaneous complex conjugate resolved spectral domain and swept-source OCT using 3×3 fiber couplers," Opt. Express 13(3), 957-967 (2005).

R. K. Wang, "In vivo full range complex Fourier domain optical coherence tomography," Appl. Phys. Lett. 90(5), 054103 (2007).

M. Yamanari, S. Makita, Y. Lim, and Y. Yasuno, "Full-range polarization-sensitive swept-source optical coherence tomography by simultaneous transversal and spectral modulation," Opt. Express 18(13), 13964-13980 (2010).

Ami Yaacobi, Jie Sun, Michele Moresco, Gerald Leake, Douglas Coolbaugh, and Michael R. Watt, "Integrated phased array for wide-angle beam steering", Opt. Lett. 39, 4575, doi: 10.1364/OL.39.004575, 2014.

Christopher V. Poulton, Matthew J. Byrd, Manan Raval, Zhan Su, Nanxi Li, Erman Timurdogan, Douglas Coolbaugh, Diedrik Vermeulen, and Michael R. Watts, "Large-scale silicon nitride nanophotonic phased arrays at infrared and visible wavelengths", Optics Letters, v. 42, No. 1, doi: 10.1364/OL.42.000021, 2017.

Christopher V. Poulton, Ami Yaccobi, Zhan Su, Matthew J. Byrd, and Michael R. Watts, "Optical Phased Array with Small Spot Size, High Steering Range and Grouped Cascaded Phase Shifters", Advanced Photonics 2016, OSA technical Digest, paper IW1B.2, doi: 10.1364/IPRSN.2016.IW1B.2, 2016.

Manan Raval, Ami Yaacobi, Daniel Coleman, Nicholas M. Fahrenkopf, Christopher Baiocco, Gerald Leake, Thomas N. Adam, Douglas Coolbaugh, and Michael R. Watts, "Nanophotonic Phased Array for Visible Light Image Projection", in EEE Photonics Conference (2016), paper MG3.4, doi: 10.1109/IPCon.2016.7831042, 2016.

K. K. Mehta and R. J. Ram, "Precise and diffraction-limited waveguide-to-free-space focusing gratings," arXiv 1607.00107,2016.

David Fattal, Zhen Peng, Tho Tran, Sonny Vo, Marco Fiorentino, Jim Brug & Raymond G. Beausoleil, "A multi-directional backlight for a wide-angle, glasses-free three-dimensional display", Nature 495, 348, 2013.

(56) References Cited

OTHER PUBLICATIONS

Martijn J. R. Heck, "Highly integrated optical phased arrays: photonic integrated circuits for optical beam shaping and beam steering". Nanophotonics, 6(1): 93-107, doi: 10.1515/nanoph-2015-0152, 2017.
Trevor K. Chan, Mischa Megens, Byung-Wook Yoo, John Wyras, Connie J. Chang-Hasnain, Ming C. Wu, and David A Horsley, "Optical beamsteering using an 8×8 MEMS phased array with closed-loop interferometric phase control", Opt Express; 21:2807-15, 2013.
M. Raval, C. Poulton, and M. R. Watts, "Unidirection waveguide grating antennas with uniform emission for optical phased arrays". Optics Letters, v. 42, No. 12, doi: 10.1364/OL.42.002563, 2017.
A. Femius Koenderink, Andrea Alù, Albert Polman, "Nanophotonics: Shrinking light-based technology", Science, v. 348, No. 6234, doi: 10.1126/science.1261243, 2015.
Mikhail I. Shalaev, Jingbo Sun, Alexander Tsukernik, Apra Pandey, Kirill Nikolskiy, and Natalia M. Litchinitser, "High-Efficiency All-Dielectric Metasurfaces for Ultracompact Beam Manipulation in Transmission Mode", Nano Letters, 15 (9), pp. 6261-6266, doi: 10.1021/acs.nanolett.5b02926, 2015.
Paul J. M. Suni, John Bowers, Larry Coldren, S.J. Ben Yoo, "Photonic Integrated Circuits for Coherent Lidar", 18th Coherent Laser Radar Conference, CLRC 2016, Jun. 26-Jul. 1, 2016.
Chao Li, Huijuan Zhang, Mingbin Yu, and G. Q. Lo, "CMOS-compatible High Efficiency Double-Etched Apodized Waveguide Grating Coupler", Opt. Expr., 21, pp. 7868, 2013.
Christopher Vincent Poulton, "Integrated LIDAR with Optical Phased Arrays in Silicon Photonics", MIT MS EECS Thesis, Sep. 2016.
S. J. Ben Yoo, Binbin Guan and Ryan P. Scott, "Heterogeneous 2D/3D Photonic Integrated Microsystems", Microsystems & Nanoengineering, v. 2, 16030; doi:10.1038/micronano.2016.30, 2016.
Francesco Aieta, Patrice Genevet, Nanfang Yu, Mikhail A. Kats, Zeno Gaburro, and Federico Capasso. "Out-of-Plane Reflection and Refraction of Light by Anisotropic Optical Antenna Metasurfaces with Phase Discontinuities", Nano Lett., 12 (3), pp. 1702-1706, doi: 10.1021/nl300204s, 2012.
Paul F. McManamon, Philip J. Bos, Michael J. Escuti, Jason Heikenfeld, Steve Serati, HuikaiXie, Edward A. Watson , "A Review of Phased Array Steering for Narrow-Band Electrooptical Systems", Proc. of the IEEE, 97, pp. 1078, doi: 10.1109/JPROC.2009.2017218, 2009.
Byung-Wook Yoo, Mischa Megens, Tianbo Sun, Weijian Yang, Connie J. Chang-Hasnain, David A. Horsley, and Ming C. Wu, "A 32×32 Optical Phased Array Using Polysilicon Sub-Wavelength High-Contrast-Grating Mirrors", Opt. Expr., 22, doi: 10.1364/OE.22.019029, 2014.
Weihua Guo, Pietro R. A. Binetti, Chad Althouse , Milan L. Mašanović, Huub P. M. M. Ambrosius, Leif A. Johansson, Larry A. Coldren, "Two-Dimensional Optical Beam Steering with InP-based Photonic Integrated Circuits," IEEE J. Sel. Topics Quantum Electron., Special Issue on Semiconductor Lasers, 19, pp. 6100212, 2013.
J. C. Hulme, J. K. Doylend, M. J. R. Heck, J. D. Peters, M. L. Davenport, J. T. Bovington, L. A. Coldren, and J. E. Bowers, "Fully Integrated Hybrid Silicon Two Dimensional Beam Scanner", Optics Express, vol. 23, No. 5 doi:10.1364/OE.23.005861, p. 5861-5874; Feb. 25, 2015.
Brian W. Krause, Bruce G. Tiemann, and Philip Gatt, "Motion Compensated Frequency Modulated Continuous Wave 3D Coherent Imaging Ladar with Scannerless Architecture," Appl. Opt, 51, pp. 8745-8761 (2012).
Fei Ding, Zhuoxian Wang, Sailing He, Vladimir M. Shalaev, and Alexander V. Kildishev, "Broadband High-Efficiency Half-Wave Plate: A Supercell-Based Plasmonic Metasurface Approach", ACS Nano, doi: 10.1021/acsnano.5b00218, 2015.
Hooman Abediasl and Hossein Hashemi, "Monolithic optical phased-array transceiver in a standard SOI CMOS process". Opt. Express 23, 6509, doi: 10.1364/OE.23.006509, 2015.
David N. Hutchison, Jie Sun, Jonathan K. Doylend, Ranjeet Kumar, John Heck, Woosung Kim, Christopher T. Phare, Avi Feshali, and Haisheng Rong, "High-resolution aliasing-free optical beam steering", Optica 3, 887, doi: 10.1364/OPTICA.3.000887, 2016.
Firooz Aflatouni, Behrooz Abiri, Angad Rekhi, and Ali Hajimiri, "Nanophotonic coherent imager", Opt. Express 23, doi 10.1364/OE.23.005117, 2015.
Tin Komljenovic, Roger Helkey, Larry Coldren, and John E. Bowers, "Sparse aperiodic arrays for optical beam forming and LIDAR", Opt. Express 25, 2511, doi: 10.1364/OE.25.002511, 2017.
Binbin Guan, Ryan P. Scott, Chuan Qin, Nicolas K. Fontaine, Tiehui Su, Carlo Ferrari, Mark Cappuzzo, Fred Klemens, Bob Keller, Mark Earnshaw, and S. J. B. Yoo, "Free-space coherent optical communication with orbital angular momentum multiplexing/demultiplexing using a hybrid 3D photonic integrated circuit", Opt Express 22, 145, doi 10.1364/OE.22.000145, 2014.
William S. Rabinovich ; Peter G. Goetz; Marcel Pruessner; Rita Mahon ;Mike S. Ferraro ; Doe Park ; Erin Fleet ; Michael J. DePrenger, "Free space optical communication link using a silicon photonic optical phased array", Proc. SPIE 9354, 93540B, doi:10.1117/12.2077222, 2015.
J. Sun, "Toward accurate and large-scale silicon photonics," MIT Ph.D. Thesis, 2013.
Drexler et al., Optical Coherence Tomography: Technology and Applications. 2nd ed. Springer International Publishing, Switzerland. 2015. Cover page and table of contents only, 9 pages.
Kerstin Worhoff, Rene M. De Ridder, B. Imran Akca, Markus Pollnau, "Silicon Oxynitride Technology for Integrated Optical Solutions in Biomedical Applications", In: 13th International Conference on Transparent Optical Networks 2011, Jun. 26-30, 2011, Stockholm, Sweden.
Dietrich, et al., In situ 3D Nanoprinting of Free-form Coupling Elements for Hybrid Photonic Integration, Nature Photonics, Apr. 2018, pp. 241-247, vol. 12, Macmillan Publishers Limited.
Muhammad Rodlin Billah, et al., Hybrid Integration of Silicon Photonics Circuits and InP Lasers by Photonic Wire Bonding, Jul. 2018, vol. 5, No. 7, pp. 876-883, Optica.
Dietrich, et al., In situ 3D Nanoprinting of Free-form Coupling Elements for Hybrid Photonic Integration, Nature Photonics, Apr. 2018, pp. 1-5, vol. 12, Macmillan Publishers Limited.
Trappen, et al. 3D-Printed Optics for Wafer-Scale Probing, 3 pages.
Amir Porat, Ori Katz, Esben Ravn Andresen, Herve Rigneault, Dan Oron, Sylvain Gigan, "Widefield Lensless Endoscopy via Speckle Correlations", Optics and Photonics News, Dec. 2016, p. 41.
Martin Ploschner, Tomas Tyc and Tomas Ciamar, "Seeing through chaos in multimode fibres", Nature Photonics, doi 10:1038/NPHOTON. 2015, Jul. 2015,112, pp. 529-538.
Tomas Cizmár and Kishan Dholakia, "Exploiting multimode waveguides for pure fibre-based imaging" Nature Communications, 3:1027, doi: 10.1038/ncomms2024, May 2012.
Martin Ploschner, Branislav Straka, Kishan Dholakia and Tomas Cizmar, "Fibre-based imaging: new challenges", Adaptive Optics and Wavefront Control for Biological Systems, Proc. of SPIE vol. 9335, 93350H, doi: 10.1117/12.2077693, Mar. 2015.
M. Ploschner, B. Straka, K. Dholakia, and T. Cizmar, "GPU accelerated toolbox for real-time beam-shaping in multimode fibres", Optics Express, 2014, vol. 22, No. 3, doi:10.1364/OE.22.002933.
Miguel A. Preciado, Michael Mazilu, Kishan Dholakia, "Multimode fibre correction for applications in optomechanics using a digital micromirror device", FTu1A.6, FiO/LS, OSA 2014.
Miguel A. Preciado, Kishan Dholakia, Michael Mazilu, "Real-time optical eigenmode characterization", FTh3G.5, FiO/LS, OSA 2014.
Reza Nasiri, Mahalati, Ruo, Yu Gu, and Joseph M. Kahn, "Resolution limits for imaging through multi-mode fiber", Optics Express, Jan. 2013, vol. 21, No. 1.
S. G. Adie, N. D. Shemonski, T. S. Ralston, P. S. Carney, S. A. Boppart, "Interferometric Synthetic Aperture Microscopy (ISAM)", In Optical Coherence Tomography: Technology and Applications. 2nd ed.; Drexler, W., Fujimoto, J. G., Eds.; Springer International Publishing, Switzerland, 2015, 965-1004, 2015.
Y. Xu, Y. Z. Liu, S. A. Boppart, P. S. Carney, "Automated Interferometric Synthetic Aperture Microscopy and Computational Adaptive Optics

(56) References Cited

OTHER PUBLICATIONS for Improved Optical Coherence Tomography", Applied Optics, 55, (8), 2034-2041, doi:10.1364/Ao.55.002034, 2016.
F. A. South, Y. Z. Liu, Y. Xu, N. D. Shemonski, P. S. Carney, S. A. Boppart, "Polarization-Sensitive Interferometric Synthetic Aperture Microscopy", Applied Physics Letters, 107, (21), DOI: Artn 211106 10.1063/1.4936236, 2015.
Aleksandar Lukic, Sebastian Dochow, Hyeonsoo Bae, Gregor Matz, Ines Latka, Bernhard Messerschmidt, Michael Schmitt, and Jurgen Popp, "Endoscopic fiber probe for nonlinear spectroscopic imaging", Optica, vol. 4, No. 5, doi: 10.1364/OPTICA.4.000496, 2017.
Ruo Yu Gu, Reza Nasiri Mahalati, and Joseph M. Kahn, "Design of flexible multi-mode fiber endoscope", Optics Express, Oct. 2015,vol. 23, No. 21, doi:10.1364/OE.23.026905.
C. Bellanger, A. Brignon, J. Colineau, and J. P. Huignard, "Coherent fiber combining by digital holography", Optics Letters, Dec. 2008, vol. 33, No. 24.
Tomas Cizmar, "Exploiting multimode waveguides for in vivo imaging" SPIE Newsroom, http://www.spie.org/newsroom/6106-exploiting-multimode-waveguides-for-in-vivo-imaging, Sep. 2015.
Yuan-Zhi Liu, F. A. South, Y. Xu, P. S. Carney, and S. A. Boppart, "Computational optical coherence tomography", https://doi.org/10.1364/BOE.8.001549, Feb. 2017.
David B. Cole, Cheryl Sorace-Agaskar, Michele Moresco, Gerald Leake, Douglas Goolbaugh, and Michel R. Watts, "Integrated heterodyne interferometer with on-chip modulators and detectors", Optics Letters, vol. 40, No. 13, Jul. 1, 2015.
Chao Zuo, Jiasong Sun, Jiaji Li, Qian Chen, "Computational microscopy with programmable illumination and coded aperture", Proceedings of the SPIE, vol. 10250, doi: 10.1117/12.2266652, 2016.
Joannis N. Papadopoulos, Salma Farahi, Christophe Moser, and Demetri Psaltis, "High-resolution, lensless endoscope based on digital scanning through a multimode optical fiber", Biomedical Optics Express, V. 4, No. 3. 2013.
Jason P. Moore and Matthew D. Rogge, "Shape sensing using multi-core fiber optic cable and parametric curve solutions", Optics Express, vol. 20, Issue 3, pp. 2967-2973, https://doi.org/10.1364/OE.20.002967, 2012.
Paul S. Westbrook, Tristan Kremp, Kenneth S. Feder, Wing Ko, Eric. M. Monberg, Hongchao Wu, Debra A. Simoff, Thierry F. Taunay, Roy. M. Ortiz , "Continuous multicore optical fiber grating arrays for distributed sensing applications", Journal of Lightwave Technology, v PP, Issue 99, pp. 1-5, doi:10.1109/JLT.2017.2661680, 2017.
Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, v 4, No, 5, https://doi.org/10.1364/OPTICA.4.000496, 2017.
J. Carpenter, B. J. Eggleton, and J. Schroder, "110×110 optical mode transfer matrix inversion", Opt. Express, vol. 22, pp. 96-101, 2014.
Joel Carpenter, "Everything you always wanted to know about Multimode Fiber", IEEE Photonics Society Newsletter, pp. 4-10, Aug. 2017.
Youngwoon Choi, Changhyeong Yoon Moonseok Kim Taeseok Daniel Yang Christopher Fang-Yen, Ramachandra R. Dasari, Kyoung Jin Lee, and Wonshik Choi, "Scanner-Free and Wide-Field Endoscopic Imaging by Using a Single Multimode Optical Fiber" Physical Review Letters, vol. 109, 203901, Nov. 2012.
Silvio Bianchi and Roberto Di Leonardo, "A multi-mode fiber probe for holographic micromanipulation and microscopy", Lab on a Chip, V. 121, 635, 2012.
T. S. Ralston, D. L. Marks, P. S. Carney, S. A. Boppart, "Interferometric synthetic aperture microscopy". Nature Physics, 3, (2), 129-134, 2007.
J. Carpenter, B. J. Eggleton, and J. Schroder, "Observation of Eisenbud-Wigner-Smith states as principal modes in multimode fibre," Nat Phot., vol. 9, No. 11, pp. 751-757, Nov. 2015.
J. Carpenter, B. J. Eggleton, and J. Schröder, "Comparison of principal modes and spatial eigenmodes in multimode optical fibre," Laser Photon. Rev., Dec. 2016.
J. Carpenter, B. J. Eggleton, and J. Schröder, "First demonstration of principal modes in a multimode fibre," in European Conference on Optical Communication, ECOC, 2014.
S. Fan and J. M. Kahn, "Principal modes in multimode waveguides," Opt. Lett, vol. 30, pp. 135-137, 2005.
J. Carpenter, B. J. Eggleton, and J. Schroder, "Complete spatiotemporal characterization and optical transfer matrix inversion of a 420 mode fiber," Opt. Lett., vol. 41, No. 23, pp. 5580-5583, 2016.
Bo Shuang, Wenxiao Wang, Hao She, Lawrence J. Tauzin, Charlotte Flateb, Jianbo Chen, Nicholas A. Moring, Logan D. C. Bishop, Kevin F. Kelly & Christy F. Landes, "Generalized recovery algorithm for 3D super-resolution microscopy using rotating point spread Functions", Scientific Reports, 6:30826, DOI: 10.1038/srep30826, 2016.
Joannis N. Papadopoulos, Salma Farahi, Christophe Moser, and Demetri Psaltis, "Focusing and scanning light through a multimode optical fiber using digital phase conjugation", Optics Express, V. 20, No. 10, 2012.
A. M. Caravaca-Aguirre, E. Niv, and R. Piestun, "High-speed phase modulation for multimode fiber endoscope," Imaging Appl. Opt. (2014).
R. Y. Gu, R. N. Mahalati, and J. M. Kahn, "Noise-reduction algorithms for optimization-based imaging through multi-mode fiber," Opt. Express 22(12), 15118-15132 (2014).
D. Loterie, S. Farahi, I. Papadopoulos, A. Goy, D. Psaltis, and C. Moser, "Digital confocal microscopy through a multimode fiber," http://arxiv.org/abs/1502.04172 (2015).
E. E. Morales-Delgado, S. Farahi, I. N. Papadopoulos, D. Psaltis, and C. Moser, "Delivery of focused short pulses through a multimode fiber", Opt. Express 23(7), 9109-9120 (2015).
Y. Choi, C. Yoon, M. Kim, W. Choi, and W. Choi, "Optical imaging with the use of a scattering lens", IEEE J. Sel. Top. Quantum Electron. 20(2), 61-73 (2014).
S. Bianchi, V. P. Rajamanickam, L. Ferrara, E. Di Fabrizio, R. Di Leonardo, and C. Liberale, "High numerical aperture imaging by using multimode fibers with micro-fabricated optics", in CLEO: Science and Innovations (OSA, 2014), paper SM2N.6.
M. Plöschner and T. Čižmár, "Compact multimode fiber beam-shaping system based on GPU accelerated digital olography". Opt. Lett. 40(2), 197-200 (2015).
A. M. Caravaca Aguirre and R. Piestun, "Robustness of multimode fiber focusing through wavefront shaping", in Latin America Optics and Photonics Conference (2014).
S. Farahi, D. Ziegler, I. N. Papadopoulos, D. Psaltis, and C. Moser, "Dynamic bending compensation while focusing through a multimode fiber", Opt. Express 21(19), 22504 22514 (2013).
R. A. Panicker and J. M. Kahn, "Algorithms for compensation of multimode fiber dispersion using adaptive optics", J. Lightwave Technol. 27(24), 5790-5799 (2009).
R. A. Horn, Matrix Analysis, 2nd ed. (Cambridge University, 2013).
24. M. Sasaki, T. Ando, S. Nogawa, and K. Hane, "Direct photolithography on optical fiber end", Jpn. J. Appl. Phys. 41(Part 1, No. 6B), 4350-4355 (2002).
Antonio M. Caravaca-Aguirre, Eyal Niv, Donald B. Conkey, and Rafael Piestun, "Real-time resilient focusing through a bending multimode fiber", Optics Express, vol. 21, No. 10, DOI:10.1364/OE.21012881, (2013).
Paul H. Beckwith, Ian McMichael, and Pochi Yeh, "Image distortion in multimode fibers and restoration by polarization-preserving phase conjugation", Optics Letters, vol. 12, No. 8, 1987.
D. Z. Anderson, M. A. Bolshtyansky and B. Ya. Zel'dovich, "Stabilization of the speckle pattern of a multimode fiber undergoing bending", Optics Letters, vol. 21, No. 11, Jun. 1996.

* cited by examiner $\ell = +1, s = +1$ $\ell = -1, s = -1$ $\ell = 0, s = +1$ $\ell = 0, s = -1$

FEW-MODE OPTICAL FIBER MEASUREMENT INSTRUMENT

CROSS REFERENCE TO RELATED APPLICATIONS

This application is a continuation of U.S. patent application Ser. No. 15/168,189, filed on May 30, 2016, entitled "Few-Mode Fiber Endoscope". The entire contents of U.S. patent application Ser. No. 15/168,189, are herein incorporated by reference.

TECHNICAL FIELD

This disclosure relates generally to endoscopic devices and in particular to an optical fiber endoscope employing few-mode optical fiber.

BACKGROUND

Medical and non-medical applications of imaging endoscopes are well known and their importance to contemporary cardiology, gastroenterology, pulmonology, laparoscopy as well as nondestructive evaluation/nondestructive testing (NDE/NDT) is widely accepted. Given that importance, improvements to endoscopic devices and systems would represent a welcome addition to the art.

SUMMARY

An advance in the art is made according to an aspect of the present disclosure directed to endoscopic devices employing few mode optical fiber.

In contrast to contemporary, prior-art endoscopic devices and systems, devices and systems constructed according to the present disclosure may employ—in addition to few-mode optical fiber—employ a variety of measurement techniques including swept-source techniques, employ widely tunable source(s), include multiple functions, and—in some embodiments—critical complex optical functions may be performed by one or more photonic integrated circuit(s).

An illustrative endoscopic system and structure according to the present disclosure includes an optical receiver selected from the group consisting of spectral domain optical coherence tomography (OCT) receiver, time domain OCT receiver, confocal receiver, fluorescence receiver, and Raman receiver; an endoscope body including fixed distal optics; and a multicore optical fiber optically coupling the fixed distal optics to the receiver.

Accordingly, and in sharp contrast to prior-art devices, devices and systems constructed according to the present disclosure may include: an optical receiver selected from the group consisting of spectral domain optical coherence tomography (OCT) receiver, time domain OCT receiver, confocal receiver, fluorescence receiver, Raman receiver, and swept-source optical coherent tomography (SS-OCT) receiver; an endoscope body including distal optics; and a few-mode optical fiber optically coupling the distal optics to the receiver; wherein the few-mode fiber optical endoscope is configured to optically illuminate a sample in one or more spatial modes and simultaneously detect multiple backscattered spatial modes from the sample and process them such that information about the sample's longitudinal optical properties is produced.

Operationally, and in further sharp contrast to prior-art devices, a method of operating a few-mode fiber endoscopic system includes directing an optical beam to a sample via an optical fiber; collecting light backscattered from the sample; directing the backscattered light to a detector via the optical fiber; and detecting the backscattered light; wherein the directed optical beam is single mode and the collected light is multiple mode. Of particular advantage, the optical fiber employed may be a few-mode optical fiber or a double-clad optical fiber—among others.

Notably, term endoscope is used throughout the disclosure to describe structures according to the present disclosure. Those skilled in the art will readily appreciate that the disclosure is not specifically limited to endoscopes. More particularly, the disclosure and underlying principles herein are equally applicable to catheters, laparoscopes, imaging guidewires as well as other medical and non-medical devices and structures. Accordingly, when the term endoscope is used, it is intended that it be interchangeable with any instrument or system used to examine the inside of something—oftentimes a body for medical reasons. Such instruments advantageously permit the interior of an organ or other cavity of the body. Of further advantage, endoscopes are capable of being inserted directly into an organ for subsequent examination.

BRIEF DESCRIPTION OF THE DRAWING

A more complete understanding of the present disclosure may be realized by reference to the accompanying drawings in which.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In the claims hereof any element expressed as a means for performing a specified function is intended to encompass any way of performing that function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

By way of some additional background, it is noted that there exist a wide variety of optical sensing technologies used in optical systems that employ single mode optical fiber. Some of these systems are interferometric in nature such as optical coherence tomography systems.

Figure 1:
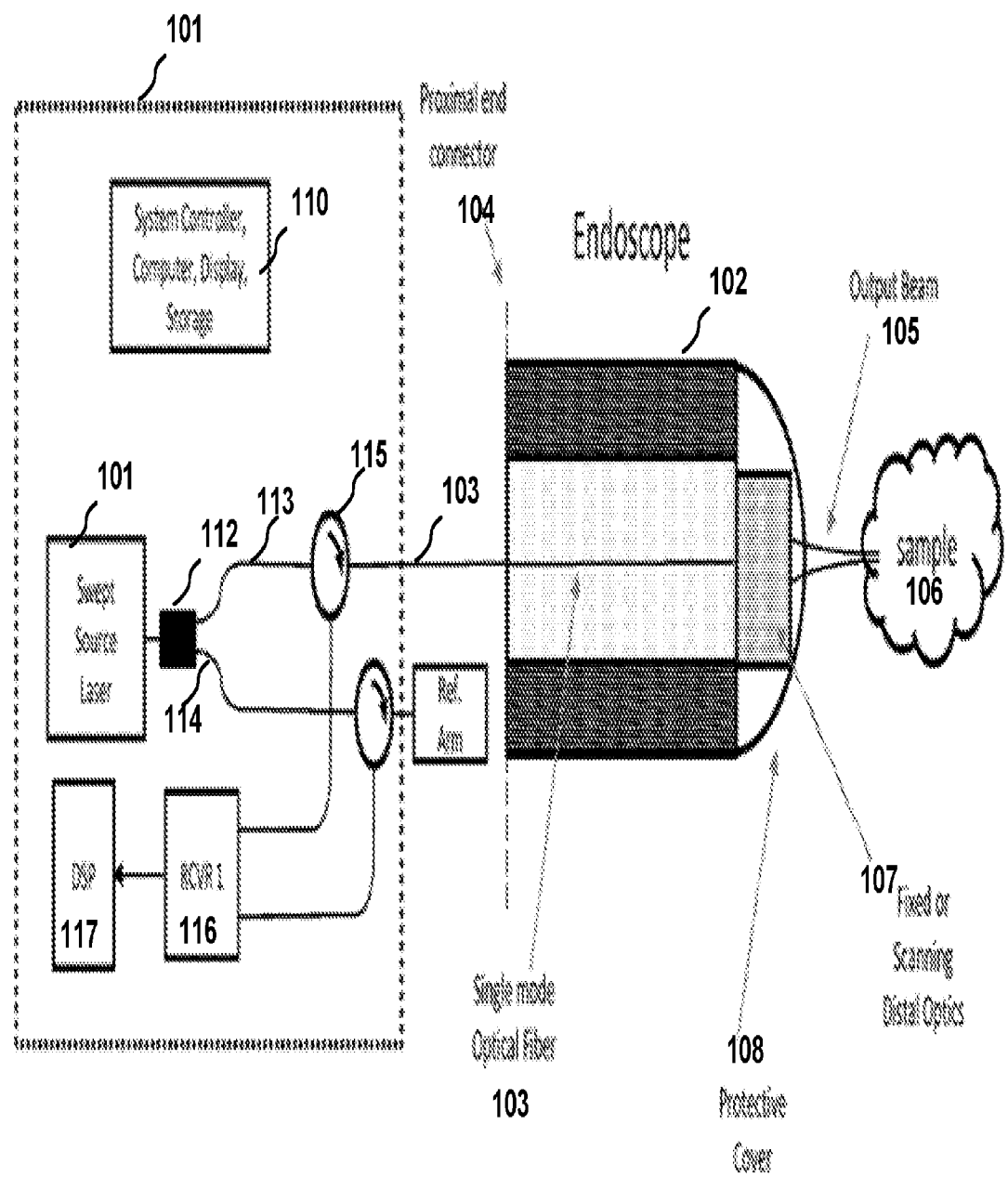
FIG. 1 shows an exemplary swept-source optical coherence tomography (SS-OCT) Prior Art endoscopic system.

Turning now to FIG. 1 there is shown a schematic of an illustrative swept source optical coherence tomography system (SS-OCT) configured as an optical endoscope such as those known in the art. As may be observed from that Figure, such an SS-OCT endoscopic system generally includes source/controller/detector sub-system 101 and an endoscope sub-systems 102 coupled together via a single mode optical fiber 103. While not specifically identified in that Figure, such endoscopes and systems may include an eyepiece, a light post, and an objective assembly. Alternative configurations may include—among other things—an access port for instrument(s) and an "umbilical" connection.

As may be readily understood by those skilled in the art, SS-OCT systems such as that shown schematically in the Figure generally include a system controller 110, a swept source laser 111, a receiver 112 and digital signal processor 113.

In the generalized illustrative schematic depicted, the controller sub system 101 is configured to operate with endoscopic sub system 102 wherein the two sub systems are coupled via single mode optical fiber 103 and proximal end connector 104.

As should be readily apparent the endoscope sub system is designed/configured such that it is readily insertable into a body cavity such that an output beam 105 may be suitably directed to sample 106. Shown further in that Figure with respect to the endoscope subsystem 102 are fixed or scanning distal optics 107 which desirably directs output beam 105 and protective cover 108 which—as its name implies—provides mechanical and other protection to the optics 107 while providing a desirable shape to the distal end of the endoscope. As should be readily understood and appreciated, a number of variations of shape, size, material and configuration are known in the art and advantageously operable in the context of systems constructed according to the present disclosure.

Operationally, the SS-OCT sub system 101 generates source light through the effect of swept source laser 101 which is split by splitter 112 and subsequently directed to sample path 113 or reference path 114. As appreciated, light directed to sample path 113 is conveyed to sample 106 by single mode optical fiber 103 and further by distal optics 107. Light back-scattered/reflected/received from sample is conveyed back to SS-OCT sub-system 101 via single mode optical fiber 103 and directed to receiver 116 and digital signal processor 117 by circulator 115 or other suitable re-directing structure(s).

At this point it is noted and should be readily appreciated that the SS-OCT system illustrated in FIG. 1 is merely illustrative of general principles of such devices. Alternative embodiments, including time domain OCT (TD-OCT), spectral domain OCT (SD-OCT) and other non-OCT modalities including both interferometric and non-interferometric are also known in the art and may be employed as application needs dictate. More particularly, fluorescence, Raman spectroscopy, near infrared spectroscopy and confocal microscopy sensing and imaging are known and understood technologies and may be employed by those skilled in the art constructing/configuring such structures/devices/systems. In addition, while FIG. 1 shows an illustrative endoscopic embodiment, alternative embodiments such as catheters, guidewires, laparoscopes, microscopes, and other embodiments/configurations are understood.

Worth noting at this point is the fact that in the prior art embodiment shown, not all the light altered and backscattered/reflected from the sample is collected from the illuminating single mode fiber. After the scattering of the source light from within the sample only that light that arrives back at the single-mode fiber which is in the fundamental mode of the single mode fiber is coupled and transmitted back to the OCT receiver. If additional modes of light could be collected and coupled to an electro-optical receiver, then additional information about the sample's optical properties could be extracted.

Figure 2:
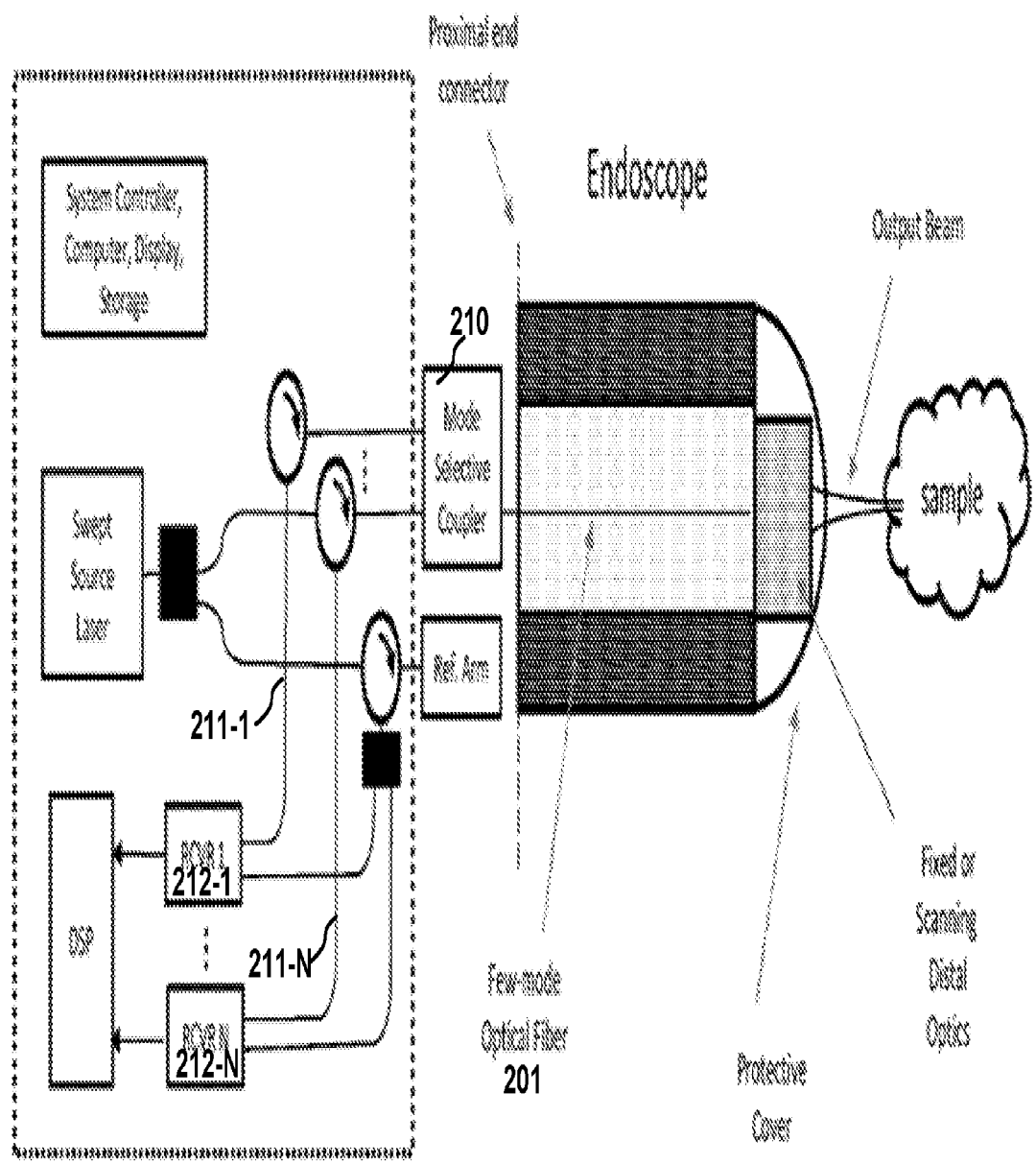
FIG. 2 shows an illustrative SS-OCT endoscopic system employing few-mode optical fiber according to an aspect of the present disclosure.

FIG. 2 illustratively shows one embodiment of an SS-OCT endoscopic system 200 according to the present disclosure that achieves multi-modal spatial detection. Notably, a few-mode optical fiber is used. Note further that while the word "few-mode" is used herein—there is no upper limit on the number of modes that are applicable to the concepts disclosed herein.

With continued reference to FIG. 2, light from swept source laser is coupled into a mode selective coupler 210 (sometimes called a mode selective photonic lantern). As will be readily understood by those skilled in the art, there exist a number and variety of types of photonic lanterns or mode selective couplers including fiber devices, free space optical devices, and fiber gratings—among others—that may be employed with structures according to the present disclosure.

Operationally—and in one particular, illustrative embodiment, the laser source light is only coupled into the fundamental circularly symmetric mode LP0 1 of the few-mode fiber. As will be appreciated, other approaches are possible and contemplated according to the present disclosure including using other modes for illumination or illuminating more than one mode simultaneously.

In the illustrative example shown, the fundamental mode of light is directed onto the sample. Back scattered light is coupled into one or more of the modes of the few-mode fiber 201, and each of those modes is separately detected by spatially extracting the modes from the few-mode fiber 201 to individual single-mode fibers 211-1 . . . 211-N through the effect of mode selective coupler 210. The individual modes are then conveyed to a number of receivers 212-1 . . . 212-N where they are detected such that information may be extracted by digital signal processor.

As will be appreciated, there exist a number of possible approaches to construct a mode selective coupler—as is known in the art—including all fiber approaches, free-space optical approaches, fiber bragg gratings, long period fiber gratings and integrated optical approaches. In the illustrative example shown in FIG. 2, the SS-OCT system employs a receiver 212-1 . . . 212-N for each mode of the few-mode fiber. Notably, one particularly attractive approach to construct a compact and low cost multiple receiver is to employ integrated optics as well as other approaches. Finally, and as noted above, there are other types of interferometric and non-interferometric optical receivers that may be employed instead of the SS-OCT embodiment shown in the Figure. Such alternatives include Raman, near-infrared spectroscopy, and fluorescence—as well as other optical modalities.

Figure 3A:
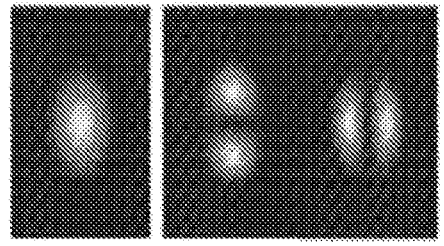
FIG. 3(A) shows several illustrative examples of near-field mode profiles of few-mode optical fiber(s)
Figure 3A:
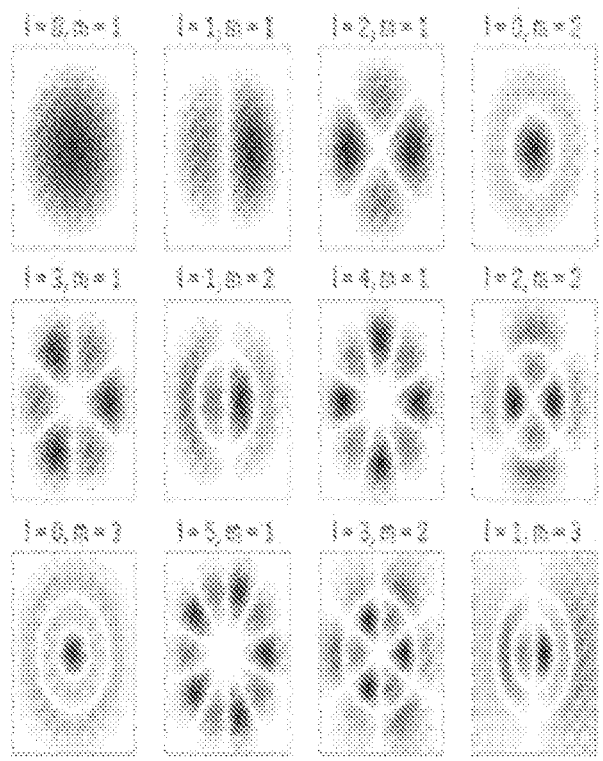

FIG. 3(A) shows some illustrative examples of near field profiles of some typical lower order modes in a few-mode optical fiber as is well known in the art. With reference to that Figure, it may be observed at the top portion shows the LP0 1 mode, the LPl1a mode, and the LPl1b mode. The bottom portion of the Figure shows additional modes that are possible according to further aspects of the present disclosure.

Figure 3B:
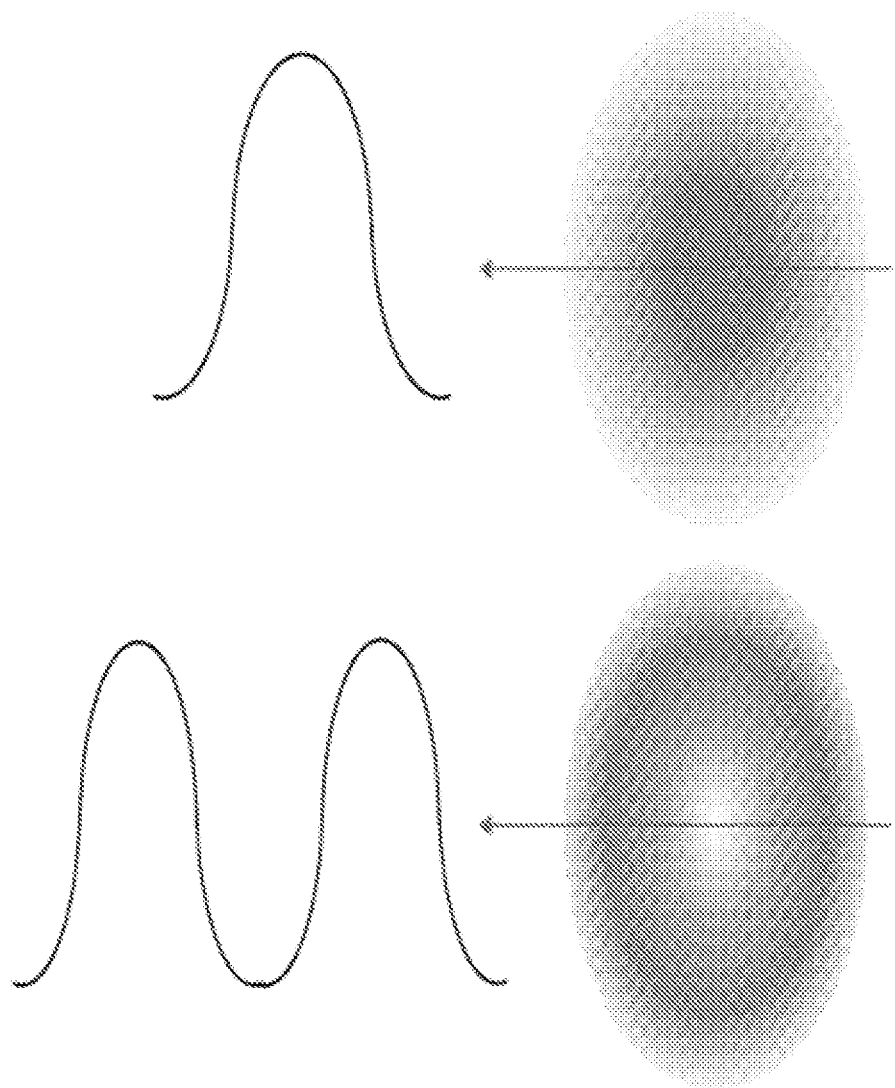
FIG. 3(B) shows an illustrative example of a circularly symmetric low-order mode and a circularly symmetric high-order mode.

In one illustrative embodiment, only two modes are utilized namely, a low-order circularly symmetric mode with a peak intensity on-axis at the beam waist and a higher-order mode that is also circularly symmetric with a null intensity on-axis at the beam waist within the sample. This is conceptually illustrated in FIG. 3(B) where the top portion of the Figure depicts the 2D peak intensity on-axis and the bottom portion of the Figure depicts the 2D null intensity on-axis. Shown further in that Figure to the left of each of the 2D intensity plots are 1D cross sections of intensity vs x-axis cuts the center. Note that one concept this Figure is intended to illustrate is that, for example a normal SS-OCT system illuminates in the LP0 1 mode in an approximate Gaussian beam profile at the beam waist within the sample. Back scattered light is coupled back into the SS-OCT receiver and axial optical profile information can be obtained about the samples optical characteristics. By also collecting a high-order mode such as shown in the bottom portion of FIG. 3(B), additional information on the samples optical properties including increased contrast imaging and obtaining additional information about the sample is possible. Such approaches are known to be beneficial in microscopy and are applied here through a few-mode fiber.

As may be appreciated, in alternative, illustrative embodiments of systems according to the present disclosure, a dual polarization OCT receiver is used for each of the detected modes since there are often two distinct polarization modes and a dual polarization receiver can implement either polarization diversity or polarization sensitive imaging as is known in the art.

Figure 3C:
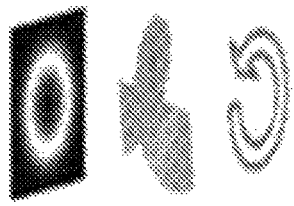
FIG. 3(C) shows illustratively four modes having distinct values of orbital angular momentum (OAM) (l) and spin (s)
Figure 3C:
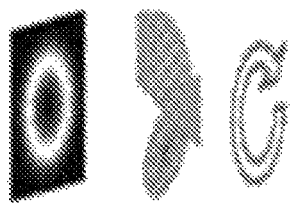
Figure 3C:
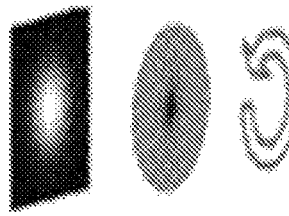
Figure 3C:
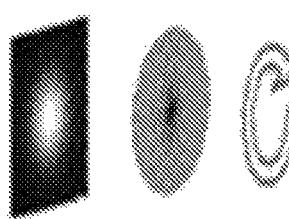

Additionally, in one illustrative embodiment of systems according to the present disclosure, orbital angular momentum (OAM) transmission and detection is utilized for obtaining additional information about the samples optical properties compared to conventional single-mode SS-OCT systems. Using OAM properties of light propagation one can create substantially orthogonal and spatially distinct patterns of light, and multiplex and demultiplex them using a mode-selective coupler-like device into separate SS-OCT receivers or other types of optical receivers. One particularly attractive property of angular momentum transmission in fiber is that some low order modes look very similar to that shown in FIG. 3B and are shown in FIG. 3C for the lower order topological charge (l) and spin (s).

As will be appreciated, there exist various approaches to multiplexing and demultiplexing OAM modes including spatial light modulators, conventional free-space optics (lenses, waveplates, polarizers, masks, etc), and fiber couplers. Additionally, there exist a variety of types of transmission fiber(s) that are suitable for propagation of OAM modes including vortex fiber, and ring fibers—among other types of multimode fibers. Advantageously, OAM beams are characterized by minimal crosstalk and orthogonality. Consequently, they are well suited for OCT and other optical sensor and imaging modalities using transmitter and receiver structures according to the present disclosure.

Figure 4:
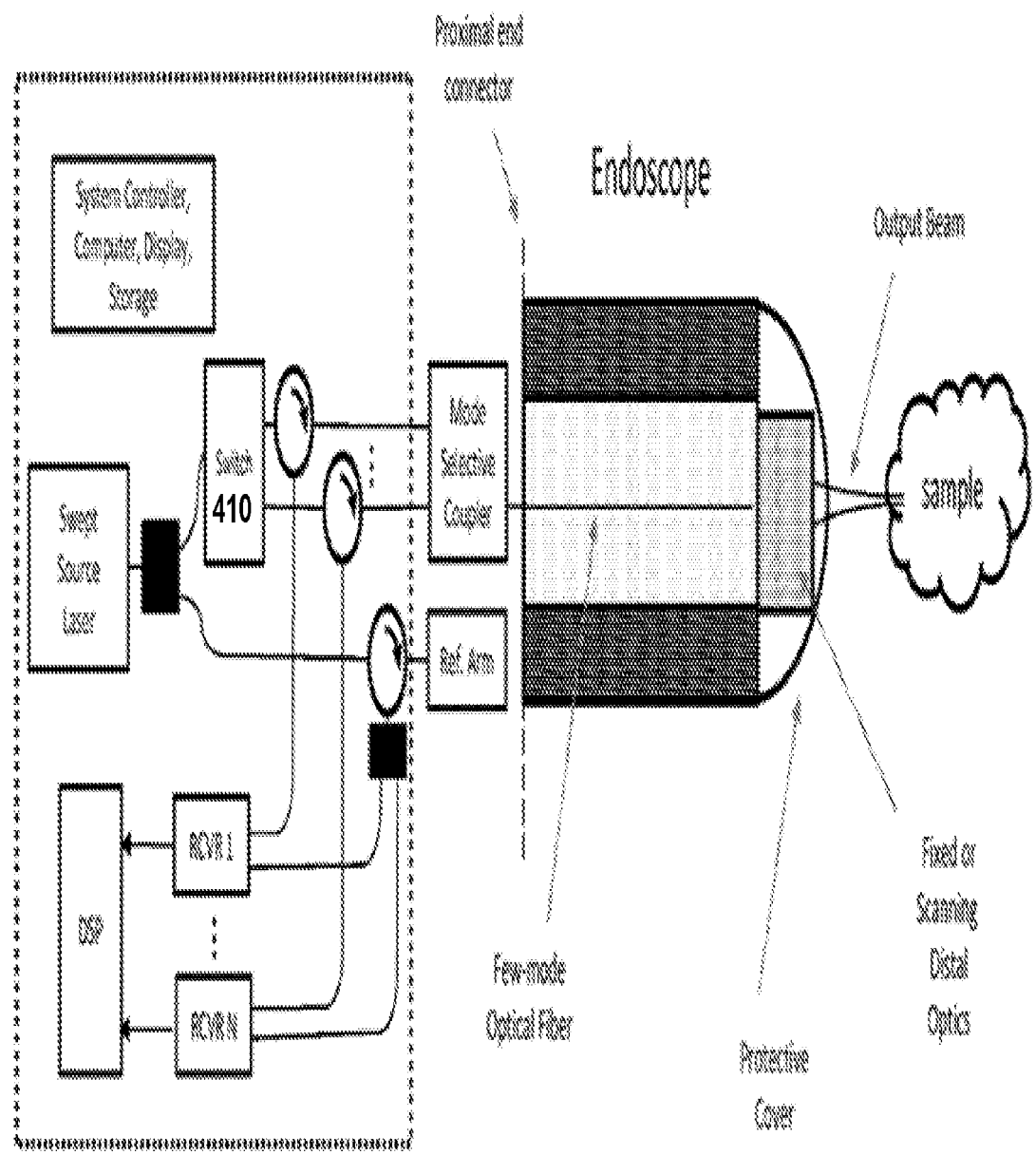
FIG. 4 shows an illustrative SS-OCT endoscopic system employing a few-mode optical fiber and a spatial switch according to an aspect of the present disclosure.

Turning now to FIG. 4, there is shown an alternative illustrative example of an SS-OCT endoscopic system 400 according to the present disclosure employing a few-mode optical fiber and a 1:N spatial switch 410 interposed between a laser source and a mode selective coupler. Advantageously, by employing such a switch, the system illustrated is capable of selecting which mode is excited on the transmitting side. Of further advantage, it also enables one to make multiple measurements of a sample's optical properties by sequentially illuminating a single transmit spatial mode and detecting multiple backscattered modes.

Figure 5:
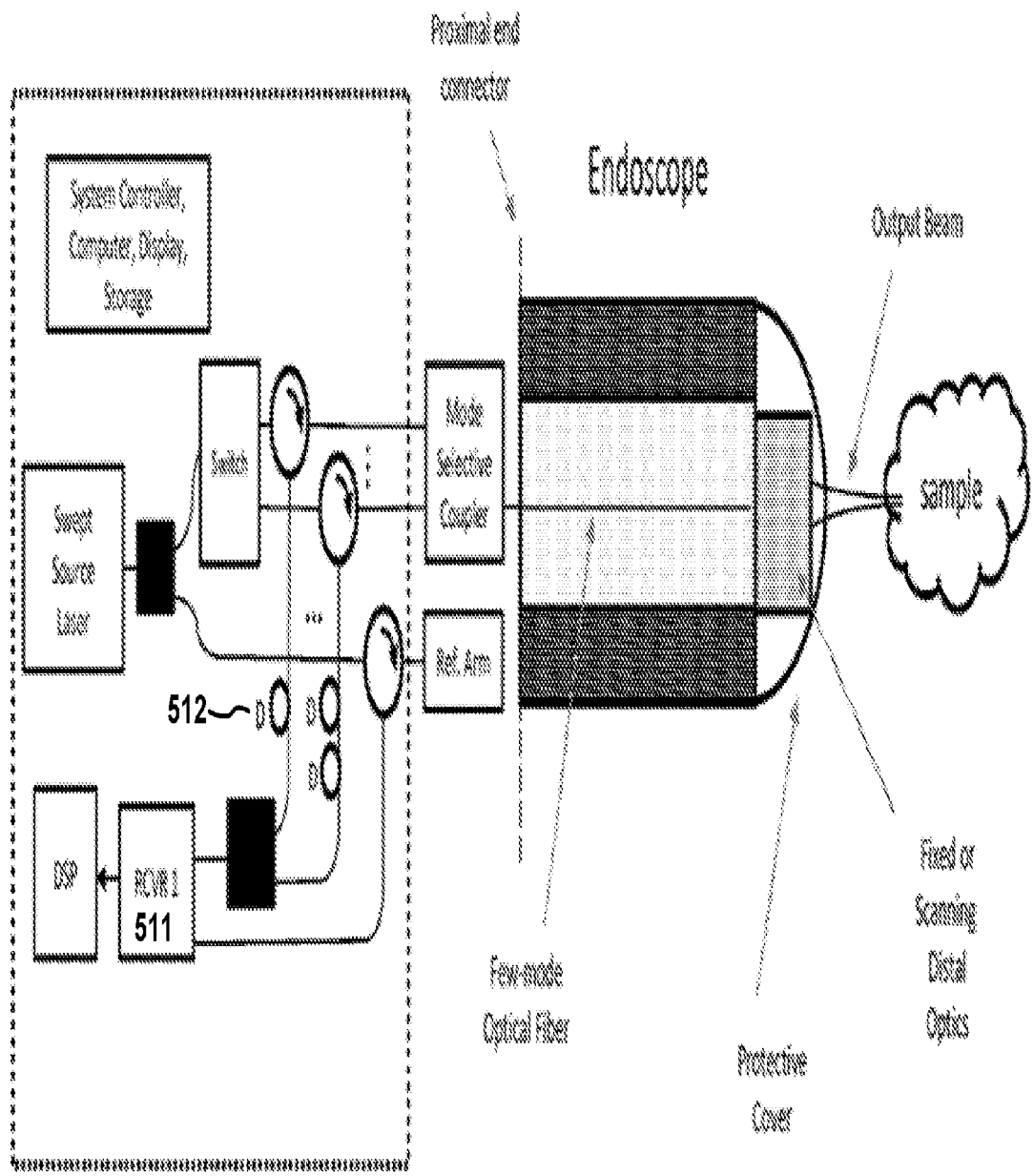
FIG. 5 shows an illustrative SS-OCT endoscopic system employing a few-mode optical fiber and a single receiver according to an aspect of the present disclosure.

FIG. 5, shows yet another illustrative embodiment of an SS-OCT system 500—similar to that depicted in FIG. 4—but only one receiver 511 is used and the information from the individual received fiber modes is uniquely delayed in time—through the effect of delay elements 512—and combined. By delaying each of the received modes "D" the information from each mode is electro-optically detected at separate and distinct i.f. frequencies. Advantageously—for the configuration depicted in FIG. 5—only one, single receiver 511 is required.

Figure 6:
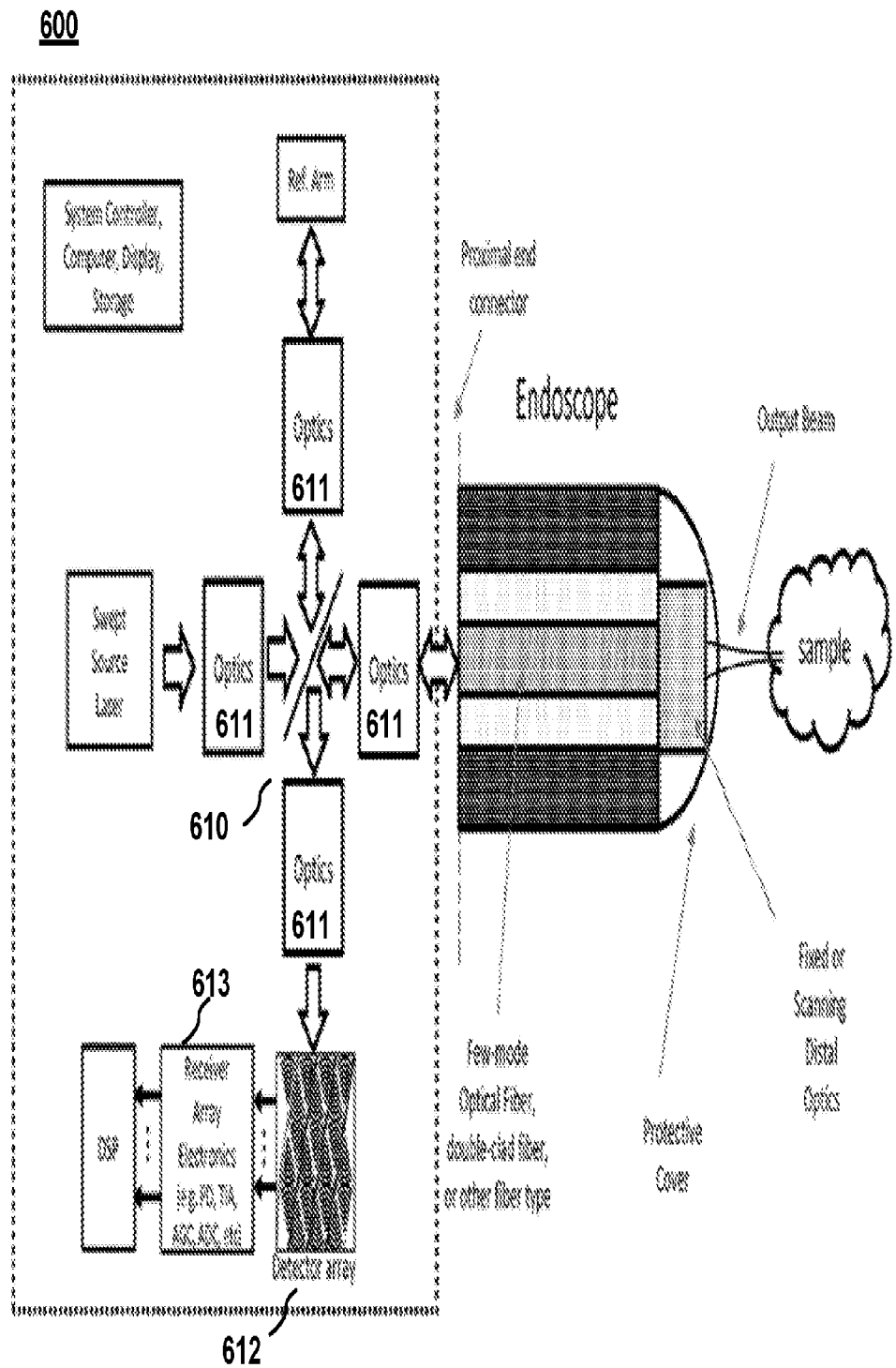
FIG. 6 shows an illustrative SS-OCT endoscopic system employing a few-mode optical fiber and a detector array according to an aspect of the present disclosure.

FIG. 6, shows another illustrative embodiment of an SS-OCT endoscopic system 600 wherein a photonic array 610 is used to implement the photonic lantern or mode selective coupler function electronically. In the illustrative example shown, the laser source is coupled into a few-mode fiber optical endoscope using bulk optical devices 611 and also light is coupled from the laser source to a reference arm. Light backscattered by the sample and reference arm are combined in a beam splitter and sent onto a detector array 612. Advantageously, there exist a variety of types/configurations of detector arrays that may be employed including a photonic integrated circuits having array(s) of surface grating couplers. The detector array 612 is in optical communication with a receiver array 613 that may include photo detectors (PDP, transimpedance amplifiers (TIAs), automatic gain control (AGC), and analog to digital converters (ADCs). The output of the receiver array is directed to a DSP unit that electronically processes the functions in a way that can mimic a mode selective coupler or many other types of functions.

Figure 7:
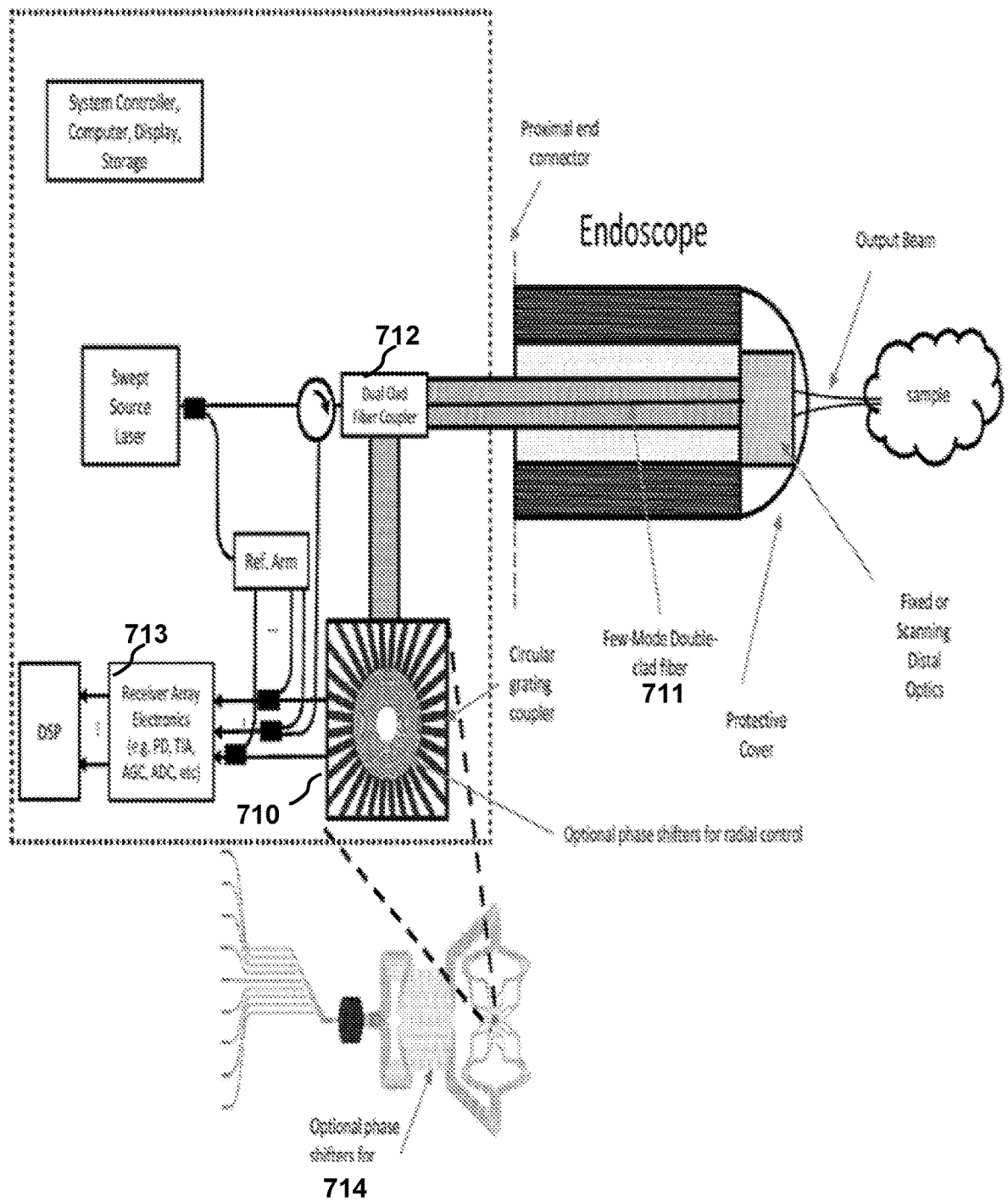
FIG. 7 shows an illustrative SS-OCT endoscopic system employing a few-mode, double-clad optical fiber and a circular grating coupler according to an aspect of the present disclosure.

Finally, FIG. 7, shows another illustrative embodiment of an SS-OCT endoscopic system 700 wherein a circularly symmetric grating coupler 710 is used along with a double clad fiber 711. As may be observed in that Figure, light from a swept laser source is coupled via single mode fiber to a dual clad fiber coupler 712. One port of the coupler contains a single mode fiber and another port contains a few-mode multimode fiber. The single mode light is coupled along the endoscope and within the single mode to the distal end and illuminates the sample. Reflected light in the same fundamental single mode is collected along with light scattered into the outer modes of the double clad fiber 711. The dual clad fiber coupler 712 directs part of this light, the light in the outer clad, to the circularly symmetric grating coupler 710 which then couples to a receiver array 713. Light from the signal mode fiber is directed via a circulator also to the receiver array 713.

As should be appreciated, such a circular grating coupler 710 may be constructed as a photonic integrated circuit using a large grating coupler that has grooves arranged in concentric circles. The grating is "fed" by an array of radially directed waveguides. These waveguides are all connected to a single input/output waveguide by one or more couplers.

Shown further are optional phase shifters 714. By placing controllable phase shifters in the waveguides, one can control the azimuthal phase distribution emanating from the grating coupler. However, one cannot control the radial phase distribution via control of the waveguide phases. If a controllable radial phase distribution is needed, then one can insert short phase shifters inside the grating coupler in a circular pattern. For example, there may be a few grating grooves, a short section of tunable phase shifter, more grating grooves, another short section of tunable phase shifter, etc. This approach extracts orthogonal angular momentum modes and is efficient for reflected light that has substantial circular symmetry. For simplicity, output wave guides shown in the exploded view of the circular grating coupler 710 are not shown coupled into the reference arm light and the receiver array. Advantageously, and as will be readily appreciated, the detector shown in FIG. 7 can also be employed for orbital angular momentum OCT as described previously.

At this point those skilled in the art will readily appreciate that while the methods, techniques and structures according to the present disclosure have been described with respect to particular implementations and/or embodiments, those skilled in the art will recognize that the disclosure is not so limited. In particular—and by way of specific example only—the SS-OCT embodiments shown herein do explicitly show lateral or rotational imaging or pull-back mechanisms as is known in the art. Of course, both proximal and/or distal active and/or passive optics are contemplated as part of this disclosure. Accordingly, the scope of the disclosure should only be limited by the claims appended hereto.

The invention claimed is:

1. A few-mode optical fiber measurement instrument comprising: (a) an optical source having an output optically coupled to a spatial mode extractor; (b) a few-mode optical fiber optically coupled to the spatial mode extractor positioned at a proximal end of the few-mode fiber, the few-mode optical fiber configured to optically illuminate in one or more spatial modes a sample positioned near its distal end using light generated by the optical source and configured to collect light from the sample positioned proximate its distal end, the few-mode optical fiber configured to support at least two spatial modes with field spatial profiles that are substantially distinct such that the light collected in the at least two spatial modes from the sample includes optical information about the sample, the few-mode optical fiber further configured to propagate the light collected in the at least two spatial modes collected from the sample to the spatial mode extractor where the propagation is such that each of the at least two optical spatial modes can be extracted; (c) the spatial mode extractor configured to extract the light collected in the at least two spatial modes and then to produce light in at least two individual modes that preserves the included spatial information about the sample, the spatial mode extractor further configured to convey one of the at least two individual light modes to a first optical directing device and another one of the at least two individual light modes to a second optical directing device, the first and second optical directing devices conveying the light in the at least two individual modes to an interferometric optical receiver; and (d) a measurement subsystem comprising the interferometric optical receiver, the interferometric optical receiver comprising a first interferometric optical receiver optically coupled to the first optical directing device and optically coupled to the optical source and configured to interferometrically detect one of the two individual light modes and a second interferometric optical receiver optically coupled to the second optical directing device and optically coupled to the optical source and configured to interferometrically detect the other one of the two individual light modes simultaneously, the measurement subsystem processing the detected light in the at least two individual modes to produce information about optical properties of the sample.

2. The few-mode fiber measurement instrument of claim 1 wherein the few-mode fiber is further configured to support at least three spatial modes, the spatial mode extractor is further configured to extract light collected in a third spatial mode to produce light in a third individual mode, and the optical receiver is further configured to detect light in the third individual mode.

3. The few-mode fiber measurement instrument of claim 1 wherein the optical source comprises a swept source laser.

4. The few-mode fiber measurement instrument of claim 1 wherein the optical source comprises a widely tunable optical source.

5. The few-mode fiber measurement instrument of claim 1 wherein the optical source conveys the source light to the distal end of the few-mode fiber in one spatial mode.

6. The few-mode fiber measurement instrument of claim 5 wherein the one spatial mode is a low-order circularly symmetric spatial mode.

7. The few-mode fiber measurement instrument of claim 1 wherein the optical source conveys light to the distal end of the few-mode fiber in more than one spatial mode.

8. The few-mode fiber measurement instrument of claim 1 wherein the light collected in the at least two optical spatial modes from the sample near the distal end of the few-mode fiber comprises light collected in a low-order mode and collected in a higher-order mode.

9. The few-mode fiber measurement instrument of claim 1 wherein the light collected in the at least two optical spatial modes from the sample near the distal end of the few-mode fiber comprises light collected in a linearly polarized mode.

10. The few-mode fiber measurement instrument of claim 1 wherein the light collected in the at least two optical spatial modes from the sample near the distal end of the few-mode fiber comprises light collected in an orbital angular momentum mode.

11. The few-mode fiber measurement instrument of claim 1 wherein the light collected in the at least two optical spatial modes from the sample at the distal end of the few-mode fiber comprises light collected in at least two distinct polarization modes.

12. The few-mode fiber measurement instrument of claim 1 wherein at least one of the at least two spatial modes having a field spatial profile comprises a field spatial profile having a null intensity on-axis at a beam waist within the sample.

13. The few-mode fiber measurement instrument of claim 1 wherein the produced information about optical properties of the sample comprises at least one of axial optical profile information, contrast imaging information, longitudinal optical property information, OCT information, image information, fluorescence information, or spectroscopy information.

14. The few-mode fiber measurement instrument of claim 1 wherein the measurement subsystem comprises at least one of a spectral domain optical coherence tomography (OCT) receiver, a time domain OCT receiver, a confocal receiver, a fluorescence receiver or a Raman receiver.

15. The few-mode fiber measurement instrument of claim 1 wherein the measurement subsystem comprises a swept-source optical coherent tomography (SS-OCT) measurement subsystem.

16. The few-mode fiber measurement instrument of claim 1 wherein the optical receiver comprises a dual-polarization optical coherent tomography receiver.

17. The few-mode fiber measurement instrument of claim 1 wherein the spatial mode extractor comprises at least one of a mode selective coupler, a grating device, or a spatial light modulator.

18. The few-mode fiber measurement instrument of claim 1 wherein the few-mode fiber is housed in an endoscope.

19. The few-mode fiber measurement instrument of claim 1 wherein at least one of the spatial mode extractor and the optical receiver is formed in a photonic integrated circuit.

20. A few-mode fiber optical measurement system comprising: (a) an optical source that generates source light; (b) an endoscope body comprising a few-mode optical fiber that is optically coupled to the optical source, the few-mode optical fiber transmitting the source light to a sample and coupling backscattered light from the sample in a low-order mode and a higher-order mode to a mode selective coupler; (c) the mode selective coupler extracting light in the low-order mode and the higher-order mode to produce light in two individual light modes and conveying one of the two individual light modes to a first optical directing device and the other one of the two individual light modes to a second optical directing device, the first and second optical directing devices directing light to an interferometric optical receiver; and (d) the interferometric optical receiver comprising a first interferometric optical receiver optically coupled to the first optical directing device and optically coupled to the optical source and configured to interferometrically detect one of the two individual light modes and a second interferometric optical receiver optically coupled to the second optical directing device and optically coupled to the optical source and configured to interferometrically detect the other one of the two individual light modes simultaneously, the optical receiver further comprising an electrical processor configured to process the interferometrically detected two individual light modes, thereby achieving multi-modal spatial detection such that information about the sample's optical properties is produced.

* * * * *